United States Patent

Toyama

Patent Number: 5,338,000
Date of Patent: Aug. 16, 1994

[54] CYLINDRICAL CONTAINER INNER SURFACE TESTER BASED ON AN IMAGE PROCESSING TECHNOLOGY

[75] Inventor: Kouichi Toyama, Kawasaki, Japan

[73] Assignee: Fuji Electric Co., Ltd., Japan

[21] Appl. No.: 970,280

[22] Filed: Nov. 2, 1992

Related U.S. Application Data

[63] Continuation-in-part of Ser. No. 914,332, Jul. 15, 1992, Pat. No. 5,233,199.

[30] Foreign Application Priority Data

Nov. 1, 1991 [JP] Japan ................. 3-286934

[51] Int. Cl.$^5$ ............................................. G01N 9/04
[52] U.S. Cl. ................................. 250/223 B; 356/240
[58] Field of Search ............... 250/559, 223 B, 223 R; 382/8, 62, 67; 358/101, 106; 356/376, 377, 240; 209/526, 524

[56] References Cited

U.S. PATENT DOCUMENTS 4,701,612  10/1987  Sturgill ......................... 250/223 B
4,943,713  7/1990  Yoshida ........................... 356/240

Primary Examiner—David C. Nelms
Assistant Examiner—K. Shami
Attorney, Agent, or Firm—Greer, Burns & Crain Ltd.

[57] ABSTRACT

The cylindrical container inner surface tester extracts image information about the opening portion and the deformation of the inner surface of a test cylindrical container through an image recognizing technique, and checks the circularity of the opening portion of the container. According to the image information, it specifies the position of a test cylindrical container as a predetermined position. Since it sequentially checks a series of cylindrical containers, the adjacent point between the containers must be identified. Then, the cylindrical container inner surface tester identifies the adjacent point of cylindrical containers through calculations and logical operations according to the image information. Likewise, the cylindrical container inner surface tester extracts a test area of an opening portion of an image of a test cylindrical container according to calculations and logical operations, and performs various processes such as determining the acceptability of the extracted white or black level of an image.

5 Claims, 37 Drawing Sheets

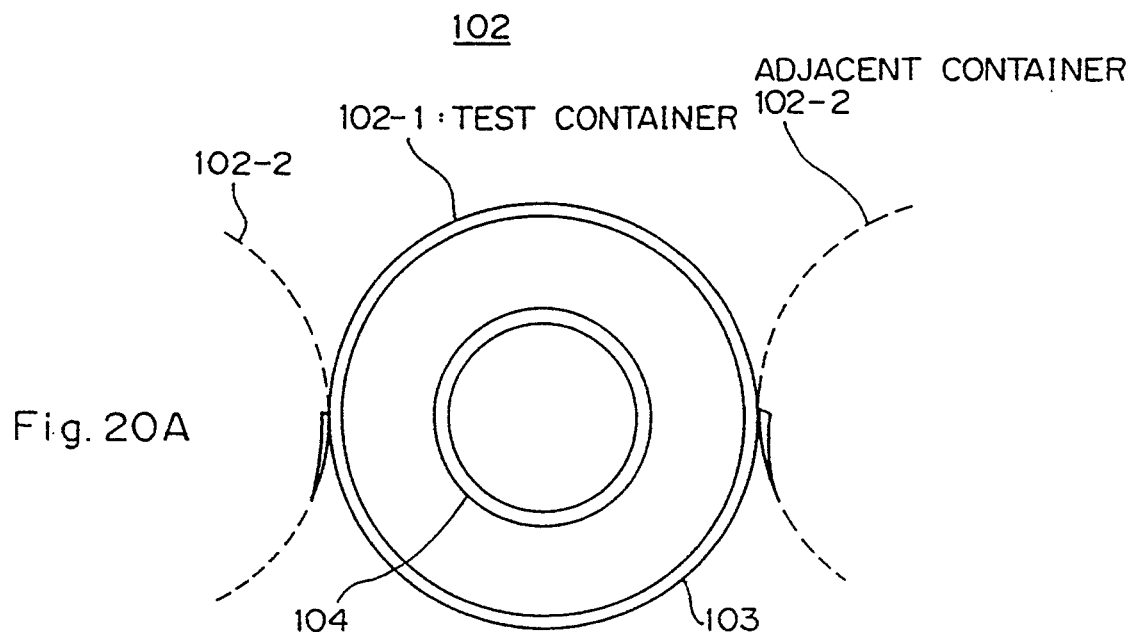
Fig. 20A
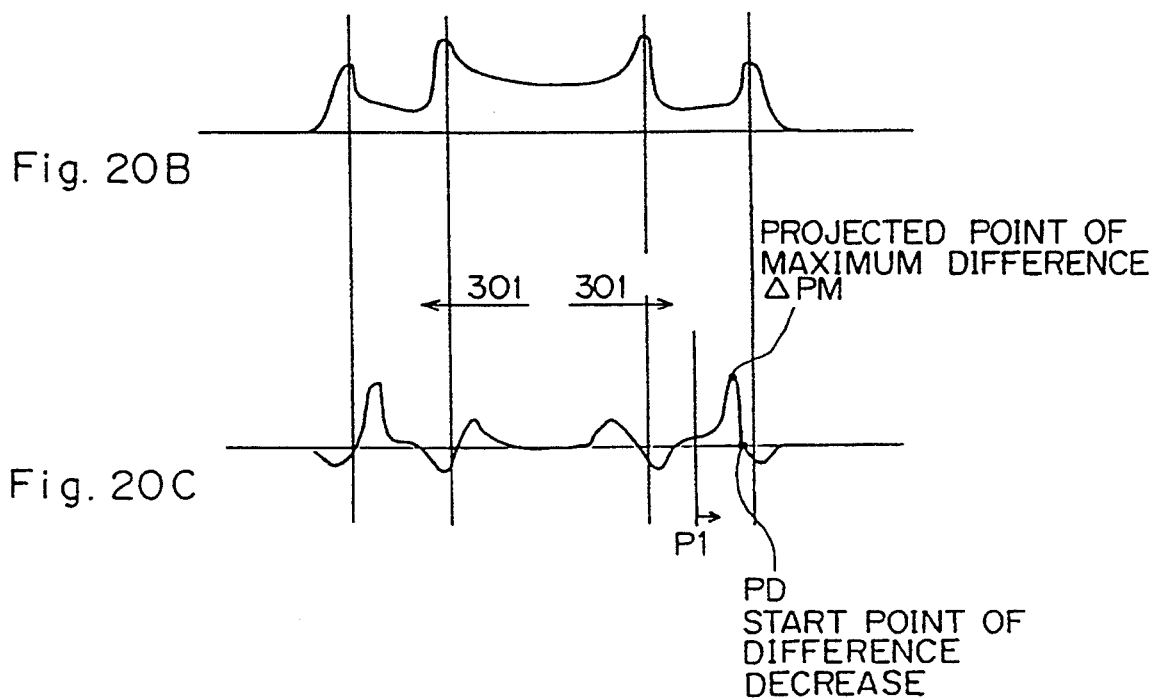
Fig. 20B
Fig. 20C

CYLINDRICAL CONTAINER INNER SURFACE TESTER BASED ON AN IMAGE PROCESSING TECHNOLOGY

CROSS REFERENCE TO RELATED APPLICATION

This application is a continuation-in-part application of U.S. patent application Ser. No. 07/914,332 filed on Jul. 15, 1992 now U.S. Pat. No. 5,233,199.

BACKGROUND OF THE INVENTION

The present invention relates to a cylindrical container inner surface tester as an image processing device for testing inner surfaces of cylindrical containers such as beer cans while being carried by a conveyer to detect foreign substances, dust, scratches, etc.

FIG. 12 is a view for explaining a highlighted portion of a sample aluminum beer can when observed from above. FIG. 12A is a top view (image) of the container (can); and FIG. 12B is its sectional view. 102 is a container; 101 is a ring-shaped illuminator for illuminating the container 102 from above; 103 is a highlighted portion at the opening of the container; and 104 is a highlighted portion of its valley. Thus, the portions 103 and 104 are highlighted at the opening and the valley of the container. They are specifically highlighted if the container has metallic raster inside.

FIG. 13B shows intensity variations represented by the scanning line Q-Q1 on the top view of the container 102 (FIG. 13A). The intensity variations can be classified into 5 level area from W1 to W5. First area W1 refers to the highlighted opening portion 103; second area W2 refers to the internal upper middle part of the container indicating comparatively high intensity; third area W3 refers to the internal lower middle part of the container subject to less amount of light of the illuminator 101 shown in FIG. 12 indicating intensity lower than other portion of the container; fourth area W4 refers to the highlighted portion of the valley; and fifth area W5 refers to the inner valley of the container.

Conventionally, these areas W1-W5 are provided with a window individually and assigned thresholds used for detecting defects such as blacks spots (black points) and white spots (white points) according to the optical characteristics of each area. One method of detecting a defect is, for example, to convert by a predetermined threshold a multi-value continuous tone image signal of 8 bits, etc. to a binary value. The signal is obtained by A/D-converting an analog video signal (analog continuous tone image signal) obtained by scanning a target image. Another method is a differentiation method in which the above described video signal is differentiated through a differentiation circuit as shown in FIG. 29 to extract a defect signal. In the differentiation method, a differentiation signal can be obtained for the contour of a test object. While either of a positive pulse or a negative pulse is generated by the differentiation along the contour of a test object, these pulses are generated simultaneously at a fine defective point, thereby extracting a defect.

That is, if the following expressions exist between the a value $P(i,j)$ and values $P(i-\alpha,j)$ and $P(i+\beta,j)$, where $P(i,j)$ indicates a target point (coordinates $x=i$ and $y=j$) referred to by a signal $P(x,y)$ obtained by differentiating an analog continuous tone image signal generated by a raster scanning operation, and $P(i-\alpha,j)$ and $P(i+\beta,j)$ indicate the points $\alpha$ picture elements forward and $\beta$ picture elements backward of the above described point $P(i,j)$ in the x direction of the scanning line.

$$P(i,j) - P(i-\alpha,j) > TH1 \text{ and}$$

$$P(i+\beta,j) - P(i,j) > TH1$$

where TH1 indicates a predetermined threshold (positive value).

A binary function values $PD(i,j)=1$ and $PD(i,j)=0$ are defined for detecting a defect on a target point and respectively indicate an abnormal black point and a normal point.

However, in the above described defect detecting method, an optimum value of a threshold TH1 to be determined by optical characteristics of a container inner surface is subject to change. Accordingly, in the conventional method, a number of concentric circle windows are necessary as shown by windows W1-W5 in FIG. 13 (five windows in this case). Simultaneously, these windows must be assigned different thresholds TH1 (and coordinates $\alpha, \beta,$). Thus, much time is wasted during the raster scanning operation, thereby offering a bottleneck to a high speed defect detection.

SUMMARY OF THE INVENTION

An object of the present invention is to provide a cylindrical container inner surface for checking a large number of cylindrical containers by quickly detecting stains and other defects such as deformations and concavities on a cylindrical container.

Another object of the present invention is to provide a high-precision cylindrical container inner surface tester for exactly detecting stains and other defects such as deformations and concavities on a cylindrical container.

A further object of the present invention is to provide a cylindrical container inner surface tester capable of detecting without fail a defective portion even though uneven illumination occurs on the inner surface of a test object.

Briefly, the objects of the present invention can be realized by providing the following configuration.

The cylindrical container inner surface tester comprises not only a conventional defect detector but also a circularity tester for checking the circularity of the opening portion of a container.

Furthermore, the cylindrical container inner surface tester comprises a test cylindrical container position specifier for selecting the orthogonal scanning line of a series of cylindrical containers to avoid the undesirable influence on images as the interference of adjacent containers during a sequential check on serially arranged test cylindrical containers, and for specifying the position of a test cylindrical container by obtaining the coordinates of the central point of the first rise point and the last fall point of a signal obtained by scanning the selected line.

Besides, the cylindrical container inner surface tester comprises a projector for performing a binary conversion on an image signal obtained by scanning an image captured from the illuminated container such that a binary image of the highlighted opening portion of the cylindrical container can be obtained, and for projecting the binary image signal in the orthogonal direction of a series of cylindrical containers. It also comprises an area identifier for obtaining the difference in the number of projected picture elements between the central point of the opening portion of the projected image obtained by the projector and another point of the image, calculating the difference in the number of projected picture elements outwards from the center, detecting the point at which the difference in the number of projected picture elements becomes larger than a predetermined threshold before the number of projected picture elements first turns negative, and identifying the adjacent point by adding a correction value to the coordinates of the detected point.

Additionally, it comprises a peak/valley defect determiner for determining a target picture element to be defective if two difference values obtained by subtracting the value of a target picture element from each of the values of two background points each being apart from said target point forward and backward each by the same number of picture elements in the same scanning line indicate the same polarity, if the absolute value of one of said two difference values is larger than a predetermined first threshold of the polarity, and if the absolute value of the other difference value is larger than a predetermined second threshold of said polarity, an image area divider for dividing according to the optical characteristics of the cylindrical container's inner illuminated surface the area of the image to be processed by the peak/valley defect determiner, and a state determinative element varying unit for varying for each of the test areas divided by the test area divider at least one of the background picture element, the first threshold, and the second threshold.

BRIEF DESCRIPTION OF THE DRAWINGS

FIGS. 20A-20C show how to detect an adjacent point according to the present invention;

DESCRIPTION OF THE PREFERRED EMBODIMENT

Figure 30A:
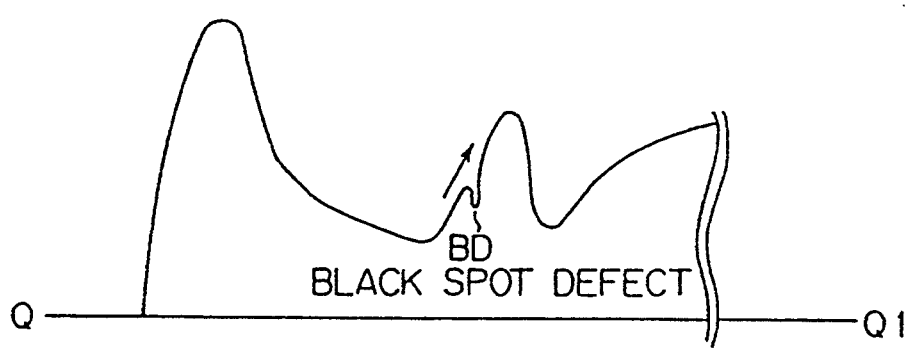
FIGS. 30A-30C show the conventional method of detecting a defect.
Figure 30B:
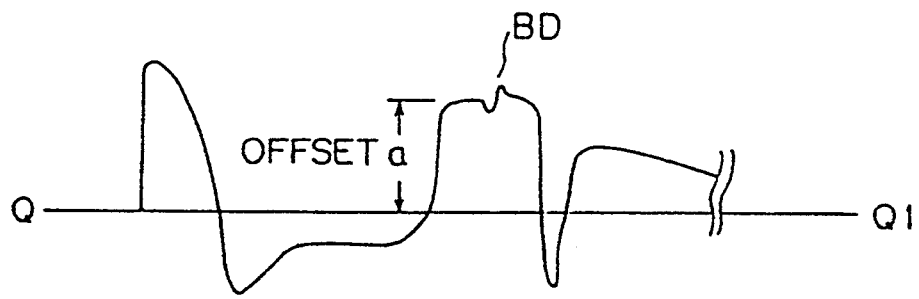
Figure 30C:

FIG. 30 is a view for explaining the problem in the conventional defect detecting method based on the differentiation method. FIG. 30A shows an example of intensity variations (analog continuous tone image signal) represented by the scanning line Q-Q1; FIG. 30B shows an example of an analog differentiation signal shown in FIG. 30A; and FIG. 30C shows an example of a digital differentiation signal shown in FIG. 30A. The portions indicated by BDs shown in FIGS. 30A-30C refer to black spots. That is, there are following problems in the conventional defect detecting method in which a black level defect BD is extracted by a signal in the area having intensity variations as shown in FIG. 30A. In the analog differentiation method, a differentiation signal indicating a small defective point is superposed on a basic intensity differentiation signal according to a time constant of a filter circuit as shown in FIG. 30B. In the digital differentiation method, a signal indicates unstable values as shown in FIG. 30C, and a differentiation signal indicating a defective point is embedded in noise components, thereby getting in difficulties in detecting a defect signal according to a predetermined threshold.

FIG. 11 is a sample top view of a container 102 having a projecting portion 102a which often generates highlighted portions 104-1, 104-2, etc. in series according to the form of the container's valley or the variations in the reflection of a light off the side of the container. Specifically, most metallic containers have a mirror like inner surface and cause the above described problems.

Such highlighted portions can be hardly removed only by appropriately using an illumination. Therefore, the conventional defect detecting method has, in vain, to solve the above described uneven illumination generated as a highlighted portion inside a test container in testing its inner surface.

An object of the present invention is to provide a cylindrical container inner surface tester for detecting a defective portion stably and precisely even though there is uneven illumination inside a test container.

To solve the above described problems, the cylindrical container inner surface tester illuminates from above in the axis direction of a container (for example, by a ring illumination 101) the inner surface of an axis-symmetrical cylindrical container (102, for example). A TV camera captures the illuminated area of the cylindrical container from above in the axis direction. Then, the captured image is analyzed by a defect detecting unit (for example, a defect detecting circuit 7, a detected defect determining circuit 12, etc.) to determine a black or white spot inside the cylindrical container.

The tester is also provided with a circularity tester (an image edge detecting circuit 6, a highlighted portion determining circuit 11, etc.) for testing the circularity of a highlighted area in the captured image, and determines the acceptability of the inner surface of the cylindrical container according to the check results of the defect detecting unit and the circularity tester (through a general determining circuit 15, etc.).

To solve the above described problems, the cylindrical container inner surface tester illuminates from above in the axis direction of a container (for example, by a ring illumination 101) the inner surface of an axis-symmetrical cylindrical container (102, for example) capable of being arranged adjacently to others in a predetermined direction (for example, in the horizontal direction). A TV camera captures the illuminated area of the cylindrical container from above in the axis direction. Then, the captured image is analyzed by a defect detecting unit (for example, a defect detecting circuit 7, a detected defect determining circuit 12, etc.) to determine a black or white spot inside the cylindrical container.

The tester comprises a scanning-line-direction position specifier (an image edge detecting circuit 6, etc.). The specifier obtains a binary image signal by performing a binary conversion, for the purpose of obtaining a binary image of the highlighted opening (103, for example) of the cylindrical container, on an image signal (for example, a multi-value continuous tone image signal PO) obtained by scanning the captured image. Then, it specifies the position of the test cylindrical container in the scanning-line direction according to the coordinates of the middle points (MA, MB, etc.) between first rise points (A0, B0, etc.) and last fall points (A1, B1, etc.) in the same scanning line of a binary image signal, among the above described binary image signals, in the area not affected by the above described adjacent arrangement (area except the area E, etc.).

In the cylindrical container inner surface tester, the above described position specifier defines an average value of a plurality of coordinates of middle points in the scanning lines as a specific value indicating the above described position.

To solve the above described problems, the cylindrical container inner surface tester illuminates from above in the axis direction of a container (for example, by a ring illumination 101) the inner surface of an axis-symmetrical cylindrical container (102, for example) capable of being arranged adjacently to others in a predetermined direction (for example, in the horizontal direction). A TV camera captures the illuminated area of the cylindrical container from above in the axis direction. Then, the captured image is analyzed by a defect detecting unit (for example, a defect detecting circuit 7, a detected defect determining circuit 12, etc.) to determine a black or white spot inside the cylindrical container.

The tester comprises a projector (a Y projecting circuit 10, etc.) and an adjacent area isolator (a process area determining circuit 14, etc.). The projector obtains a binary image signal by performing a binary conversion, for the purpose of obtaining a binary image of the highlighted opening (103, for example) of the cylindrical container, on an image signal (for example, a multi-value continuous tone image signal PO) obtained by scanning the captured image. Then, it projects the above described binary image signal in the direction perpendicular to the above described adjacent arrangement direction (in the Y direction, etc.). The adjacent area isolator obtains the difference in the number of image elements between the normal image and the projected image, checks the difference in the number of picture elements from the center of the image of the cylindrical container to its circumference (to the opening of the container), detects a point where the difference in the number of picture elements exceeds a predetermined threshold (for example, the maximum difference projection point ΔPM) in the area from the center to a point where the difference in the number of picture elements first falls to a negative, adds a predetermined correction value (β, for example) to the coordinates of the detected point, and extracts the above described adjacent arrangement area using the resultant coordinates.

To solve the above described problems, the cylindrical container inner surface tester illuminates from above in the axis direction of a container (for example, by a ring illumination 101) the inner surface of an axis-symmetrical cylindrical container (102, for example). A TV camera captures the illuminated area of the cylindrical container from above in the axis direction. Then, the captured image is analyzed to determine a black or white spot inside the cylindrical container.

The cylindrical container's inside surface tester comprises a defective peak/valley determiner (for example, an antecedent of an AND gate in a peak/valley detection and binary-conversion circuit 24), an image test area divider, and a value changer.

The defective peak/valley-determiner determines that a target picture element indicates a defect if two differences obtained by subtracting the value (for example, PO(i,j)) of a target picture element in the same picture element scanning line for a continuous tone image signal (test area continuous tone image signal 23a, etc.) which is obtained by scanning the above described captured image from the values (PO(i+$\alpha$,j), PO(i-$\beta$,j), etc.) of two background picture elements (hereinafter referred to as a forward background picture element and a backward background picture element respectively) a predetermined number of picture elements (hereinafter referred to as picture elements) backward or forward of the target picture element indicate the same polarity, if an absolute value of one of the above described two differences is larger than a predetermined first threshold (THD, for example) corresponding to the polarity, and if the other absolute value is larger than a predetermined second threshold (THD, for example).

The divider divides (into Z1-Z4, Za-Zc, etc.) the test area of a target image of the defective peak/valley determiner according to the optical features of a cylindrical container inner surface illuminated by the above described illuminator.

The value changer changes at least one value among the number of the above described picture elements, the first threshold, and the second threshold.

The tester comprises a frame memory for storing as the data for the above described captured image a multi-value continuous tone image signal A/D-converted from a continuous tone image signal obtained by scanning the captured image, and an area detecting unit for generating a binary image signal by binary-converting using a predetermined threshold a multi-value continuous tone image signal read by horizontally or vertically scanning the frame memory and for determining as a test area the area between the first rise point and the last fall point of each scanning line of the binary image signal.

Another cylindrical container inner surface tester according to the above described tester further comprises a masking unit for masking using predetermined mask pattern data an area different in optical characteristics from that in a test area detected by the area detecting unit.

Another configuration is described below.

The captured image is analyzed to determine a black or white spot inside the cylindrical container. The image of the inner surface of the cylindrical container is scanned along a ring or spiral scanning line (hereinafter referred to as a circular scanning line) which is centered on the center of the image and varies sequentially per cycle of a radius varying every one or more picture elements predetermined. Then, the absolute value indicating the difference between the intensity of the target picture elements among a plurality of picture elements arranged at intervals such that one or more picture elements are arranged between two target picture elements and the intensity of background picture element predetermined number of a plurality of picture elements forward or backward of the target picture element is compared with a threshold predetermined according to the position of the circular scanning line. The above described processes are repeated for each target picture element, and a determining unit determines a defective container inner surface when an absolute value larger than the value of the difference between the above described intensity values is detected.

The above mentioned threshold must be set as the optimum threshold per circle of the circular scanning line.

The intensity of the background picture element refers to an average intensity value among the picture elements in a predetermined one- or two-dimensional local area centered on the background picture element.

Defects can be detected precisely by divisionally extracting highlighted portions after a binary conversion and checking the circularity of the divisionally extracted patterns to collectively detect the deformation, irregular concave, and black dust spots on test objects. Then, black and white spots are checked concurrently in the same window area, thereby reducing the number of window areas and performing the whole process at a high speed.

An average value of the coordinates of middle points between first rise points and last fall points in the same scanning line of a binary image signal in the area not affected by the above described adjacent arrangement is obtained to specify the position of a test cylindrical container prior to this circularity check.

The projected amount of the binary image of the highlighted portion at the opening projected in the direction perpendicular to the adjacent arrangement of containers is obtained to isolate a test area from the area of an adjacent container. Then, the difference between the normal image and the projected image is searched for from the center to the edge of the container so that the adjacent point can be detected.

A target picture element value and two background picture element values are extracted. The target picture element value (coordinates x=i and y=j) at a target point PO(i,j) are associated with a multi-value continuous tone image signal PO(x,y) based on the raster scanning operation. The background picture element values of two background points PO(i+$\alpha$,j) and PO(i-$\alpha$,j) indicate the values of the points each being positioned at $\alpha$ picture elements forward and backward of the above described point PO(i,j) in the x direction of the scanning line are extracted. Then, the intensity relationship where the relationship among these three points indicates a valley when detected as a black level while it indicates a peak when detected as a white level is detected (that is, the difference in intensity between a background picture element value and a target picture element value is detected). The target picture element value PO(i,j) is determined to be a picture element indicating a defect when the absolute value indicating the difference in the intensity exceeds a predetermined threshold THD.

Figures 22A, 22B:
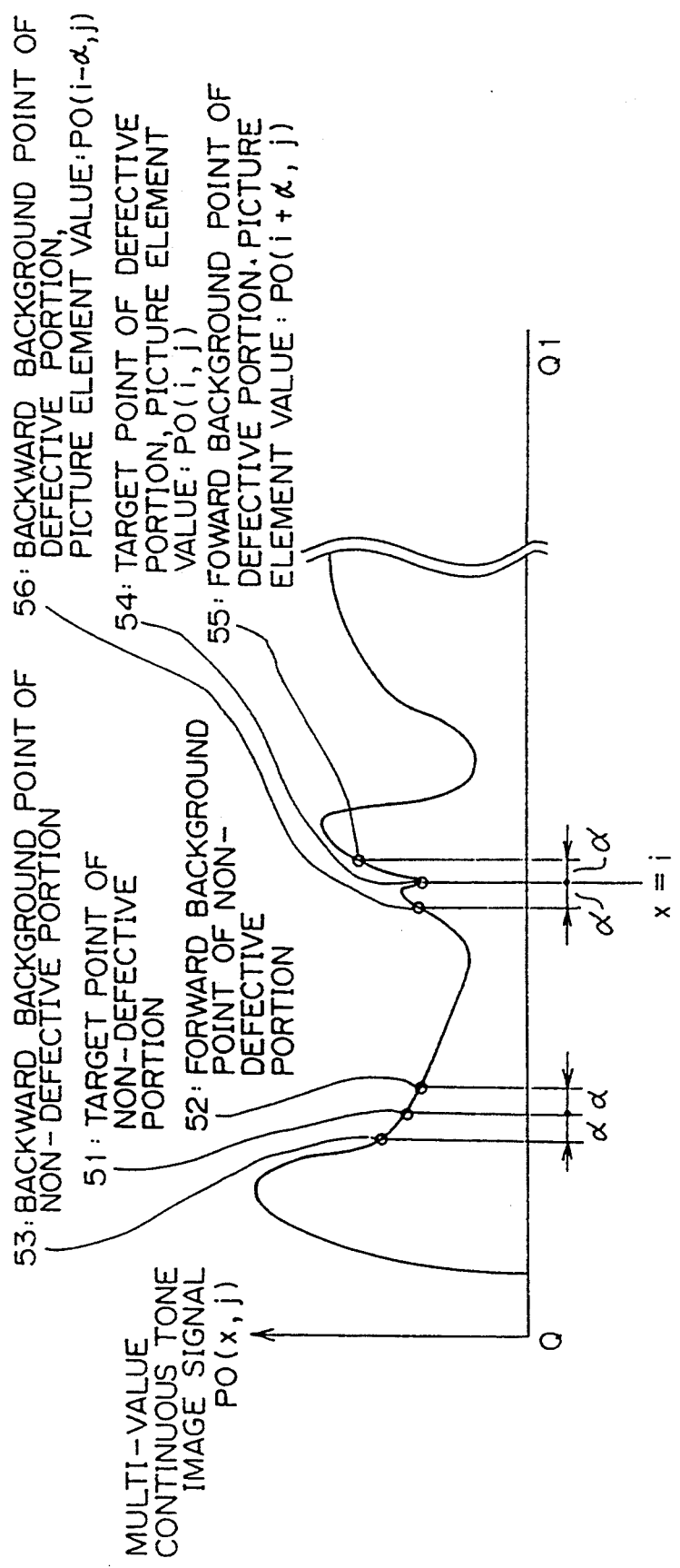
FIGS. 22A and 22B show the principle of the method of detecting a valley and performing a binary conversion.

FIG. 22 shows the principle of the valley-detection binary-conversion method which is the most important point in the present invention. FIG. 22A shows an example of a multi-value continuous tone image signal PO(x,y) in the scanning line Q-Q'i (y=j), where 51 is a target point in a non-defective portion; and 52 and 53 are forward background point and backward background point of a non-defective portion each being a picture elements forward and backward of the target point 51 in the scanning line.

Likewise, 54 is a target point in a defective portion; and 55 and 56 are forward background point and backward background point of a non-defective portion respectively a picture elements forward and backward of the target point 51 in the scanning line.

If the following expressions exist when the coordinates of a target point are (i,j) (that is, x=i and y=j), a binary function value POD(i,j)(referred to as a binary defective peak/valley image signal) for detecting a defect on a target point equals 1, and the target point is determined to be a valley (detect).

$$PO(i-\alpha,j) - PO(i,j) > THD \quad (1)$$

and $$PO(i+\alpha,j) - PO(i,j) > THD \quad (2)$$

where THD indicates a predetermined threshold (positive value).

The non-defective portion shown in FIG. 22 does not apply to the above described expression (2), and no defects are detected. However, expressions (1) and (2) exist in the defective portion shown in FIG. 22 and a valley defect is detected. FIG. 22B shows the above described peak/valley binary image signal POD (x,j) as an output of defect determination.

Thus, an optimum detecting performance can be realized by dividing the waveform shown in FIG. 22A into a plurality of small areas and appropriately assigning to each of the small areas a threshold THD and the number $\alpha$ of picture elements indicated in expression (1) and (2) above.

When a peak (defect) is detected by the present invention, the target point is determined to be a defective peak having the peak/valley binary image signal POD-(i,j)=1 if the following expressions exist where the position of the difference paragraph in each of the above described expressions (1) and (2) is exchanged with the other paragraph as follows.

$$PO(i,j) - PO(i-\alpha,j) > THD \quad (1A)$$

and $$PO(i,j) - PO(i+\alpha,j) > THD \quad (2A)$$

Figure 13A:
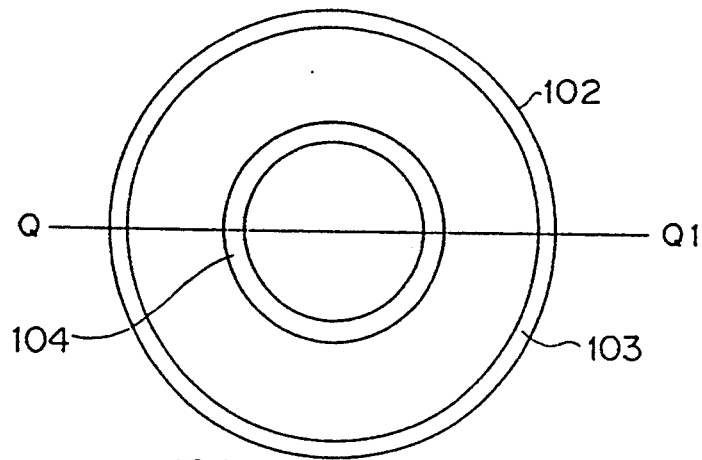
FIGS. 13A and 13B show the relationship between the intensity variations inside a cylindrical container and the conventional division of a window.
Figure 13B:
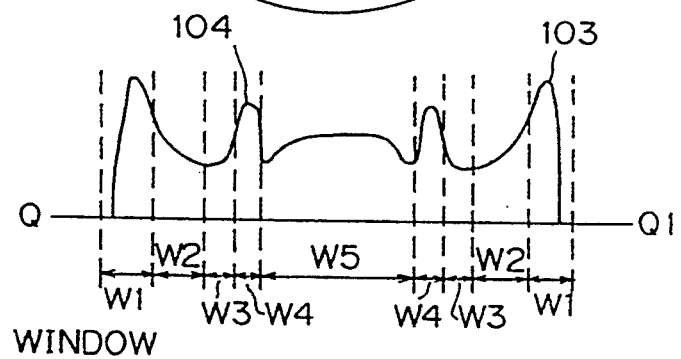

The tester for easily detecting defective concaves illuminates from above in the axis direction of a container the inner surface of an axis-symmetrical cylindrical container using a ring-shaped illuminator. When a TV camera captures the illuminated area of the cylindrical container from above in the axis direction and the captured image is analyzed, the distribution of the continuous tone on the container inner surface is concentrically generated as shown in FIGS. 13A and 13B. Taking this into account, a picture element string is obtained by scanning the container inner surface along the ring or spiral circular scanning line. When a defective concave exists, it appears as a continuous tone in the scanned picture element string. Thus, the absolute value ΔP indicating the difference between the intensity P0 of the target picture elements in a scanned picture element string and the intensity P1 of the background picture element d picture elements forward or backward of the target picture element is calculated by the following equation.

$$\Delta P = \| PO \|$$

A threshold THP is assigned to each of the windows W1 through W5 shown in FIG. 13B, and the threshold THP is compared with the absolute value ΔP indicating the difference between the intensity values. If ΔP is larger than the THP, the target picture element is determined to be a picture element of a defective inner surface such as a concave, etc.

However, the threshold THP can be set per circle of the circular scanning line, for example, according to its position. The intensity P1 of the background picture element can be an average intensity value among picture elements in a one-dimensional local area (that is, a series of n picture elements on the scanning line) or a two-dimensional local area (that is, a local area comprising n picture elements by n picture elements).

Figure 1:
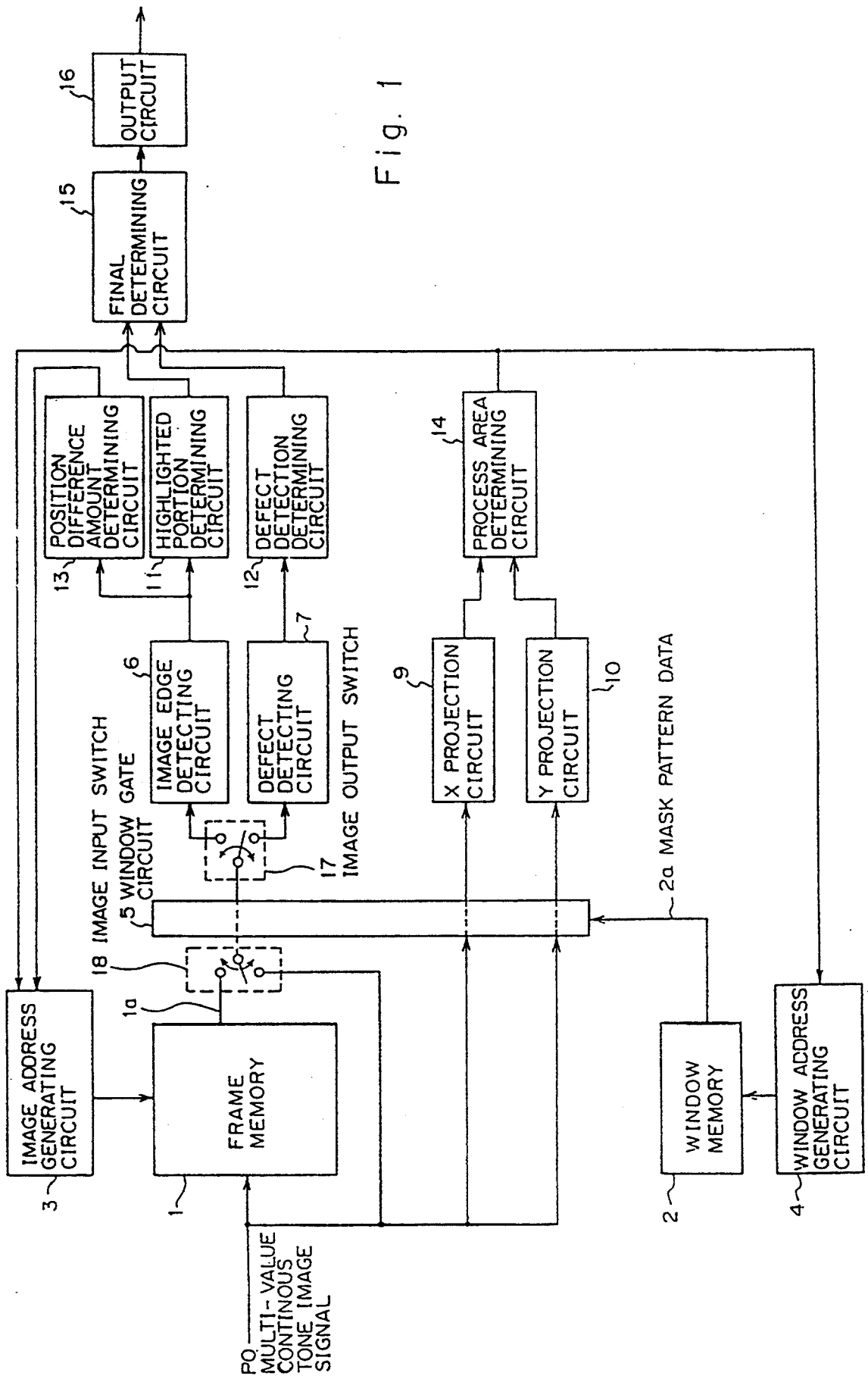
FIG. 1 is a block diagram of the hardware configuration of the first embodiment of the present invention.
Figure 21:
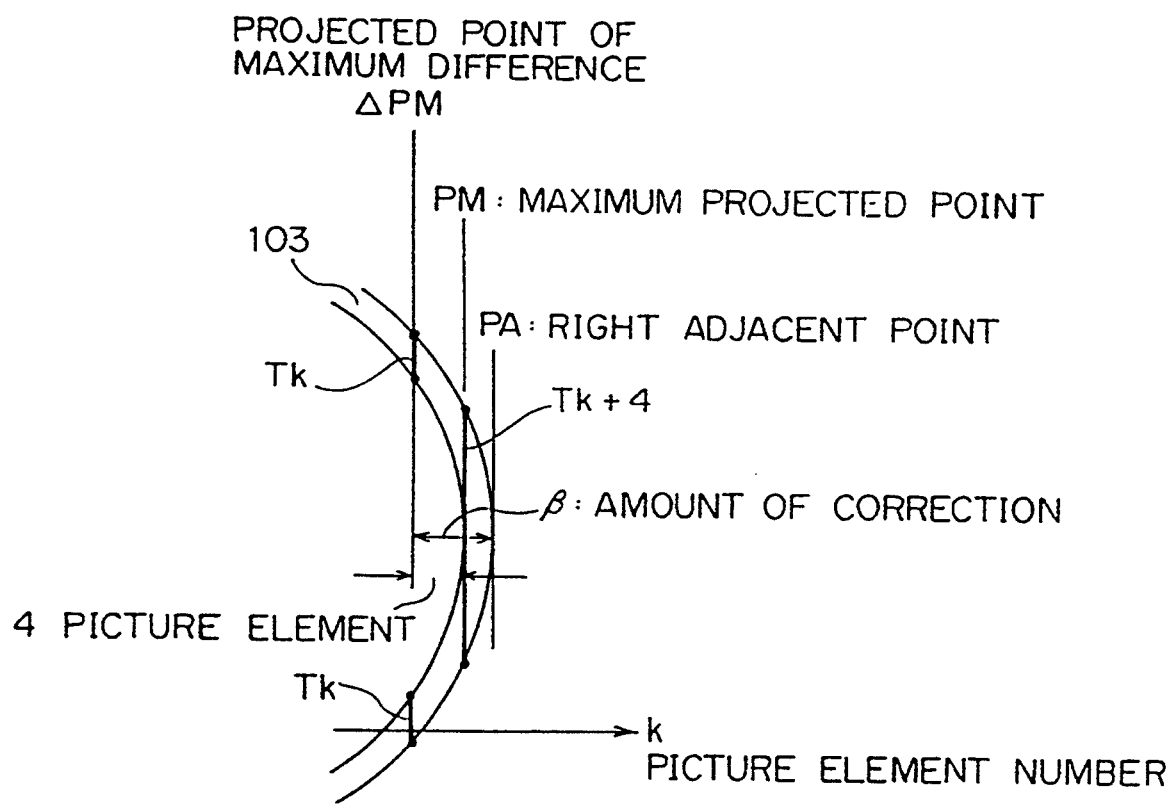
FIG. 21 is an enlarged view of FIG. 20.

An embodiment of the present invention is explained by referring to FIGS. 1 and 21. FIG. 1 is a block diagram of hardware as an embodiment of the present invention. In FIG. 1, PO is a multi-value (example, 8-bit, for example) continuous image signal generated by AD-converting a video signal obtained by raster-scanning a screen of a TV camera; a frame memory 1 receives this multi-value continuous tone image signal PO and stores it as a piece of multi-value screen data; and an address generating circuit 3 generates addresses for the frame memory 1. A window memory 2 stores a mask pattern prepared for each window; an address generating circuit 4 generates addresses for the window memory 2; and a window gate circuit 5 masks a multi-value continuous tone image signal PO or an image signal 1a read from the frame memory 1 with a mask pattern data 2a from the window memory 2, and passes the image signal PO or the image signal 1a in a specified window area.

An image input switch 18 selectively switches either to the multi-value continuous tone image signal PO or to the frame memory image signal 1a. The switch 18 applies to an image edge detecting circuit 6 the latest multi-value continuous tone image signal PO in parallel with an input of the signal PO to the frame memory 1 so that a position difference amount determining circuit 13 described later can be operated.

An image output switch 17 switches an output image signal from the image input switch 18 received through the window gate circuit 5 to the image edge detecting circuit 6 or a defect detecting circuit 7.

The image edge detecting circuit 6 detects the edge of an image, that is, the outer point (point in an outer circumference) and the inner point (point in the inner circumference) of a ring-shaped highlighted portion. In the detecting operation, an inputted image signal is converted into binary data using a threshold predetermined for detecting the position of a target image and for use in a circularity test, etc. Then, the coordinates of rise points and fall points of the binary signal are stored as image edge data in a memory (6A through 6D described later by referring to FIG. 8) of the image edge detecting circuit 6.

A circuit 11 checks the circularity on the coordinates of the points in an outer or inner circumference detected by the image edge detecting circuit 6.

To open a window at the right position relative to a target image, the position difference amount determining circuit 13 detects the difference amount between the center of the current target image detected by the input of the latest multi-value image signal PO from the image edge detecting circuit 6 and the center of a predetermined window.

The defect detecting circuit 7 detects a defect (black or white spot) by the differentiation method described in the prior art technology and calculates an area, etc. A defect detection determining circuit 12 compares a detection result of the circuit 7 with a predetermined value to determine the acceptability.

An X projection circuit 9 obtains an X-direction projection pattern of a target image using a multi-value image signal PO received through the window gate circuit 5. Likewise, a Y projection circuit 10 obtains a Y-direction projection pattern of a target image. A process area determining circuit 14 determines the image area of a test container not adjacent to images of other containers using the data outputted from the two projection circuits 9 and 10.

A final determining circuit 15 receives determination results from the highlighted portion determining circuit 11 and the defect detection determining circuit 12 to give a final determination. An output circuit 16 indicates the acceptability of a test container according to an output determination signal outputted by the final determining circuit.

Figure 4A:
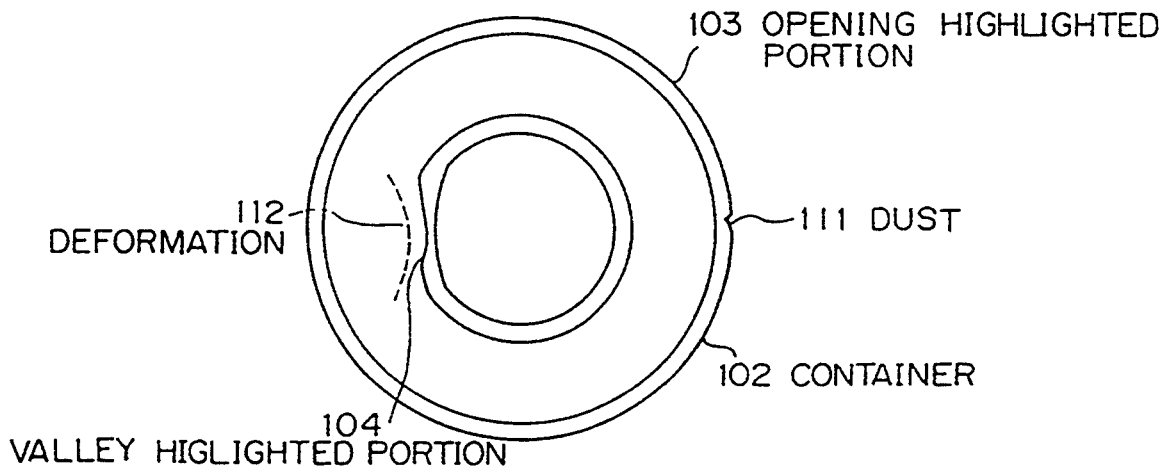
FIGS. 4A and 4B show the influence of a defective inner surface of a container on a highlighted portion.
Figure 4B:
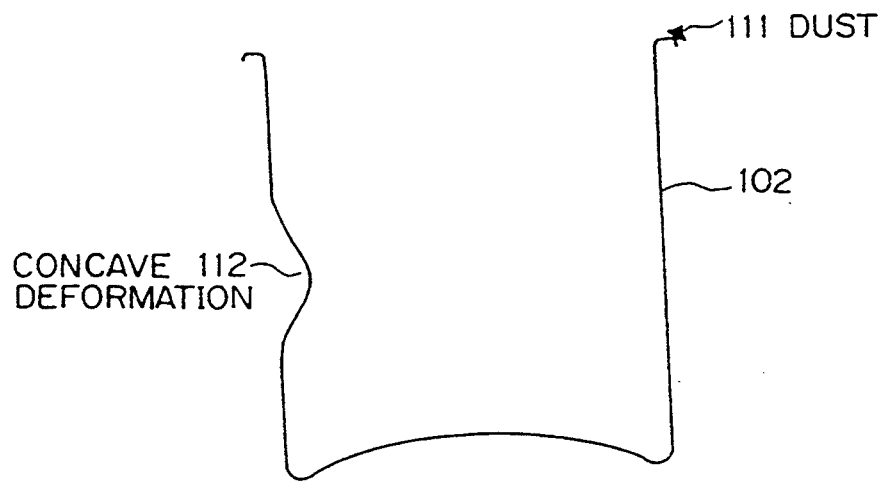

FIG. 4 shows the influence of a defect in the highlighted portion of a can, which has a defect in the inner surface, observed from above FIG. 4A is a plan view; and FIG. 4B is a sectional view. When there is dust detected at the opening of a container 102, it is detected as a lack in a circumference which indicates the highlighted portion 103 at the opening as shown in FIG. 4A. If there is a big concave deformation 112 on the side of a container, it can be detected as a deformation in the highlighted valley portion 104. However, unlike dust, etc., since a concave deformation indicates a small contrast difference, the concave deformation 112 can be easily detected by the circularity check performed on the highlighted valley portion 104.

Figure 5:
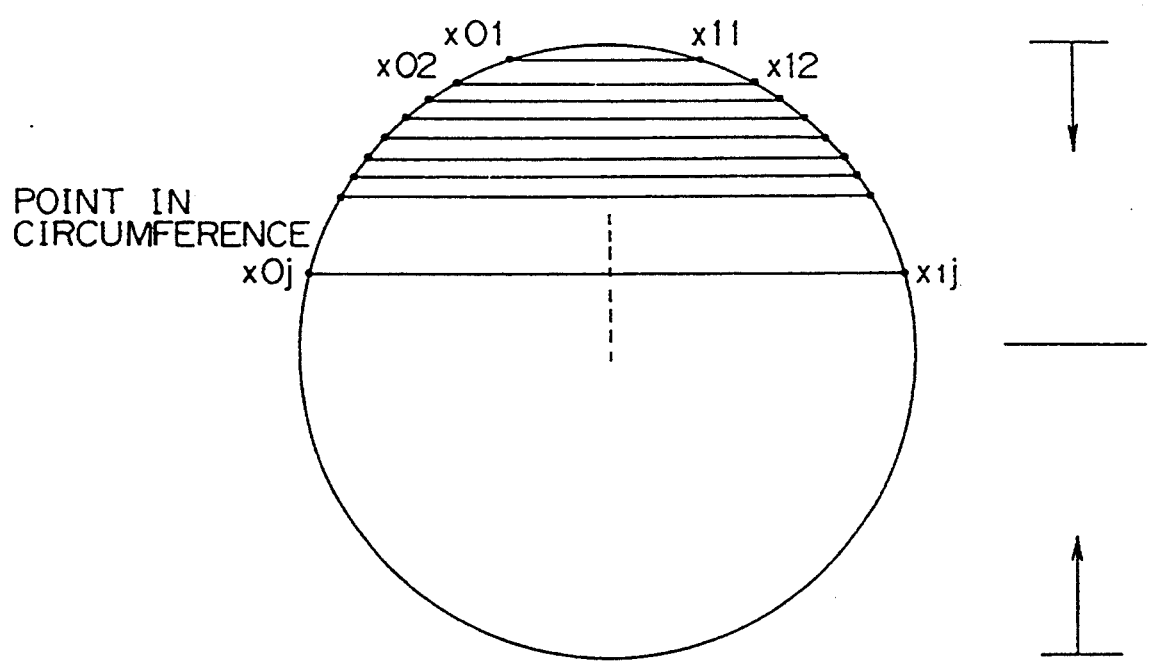
FIG. 5 is a view of points in the circumference of a highlighted portion which are used in a circularity test.

FIG. 5 is a view for explaining the circularity detecting method operated by the highlighted portion determining circuit 11. In FIG. 5, "x0j" and "x1j" respectively indicate a rise point and a fall point of coordinates of a point in an outer circumference which indicates a highlighted portion of a non-defective container (where j=1,2, ..... that is, j is a parameter corresponding to a coordinate of "y" in the horizontal scanning line). First, the coordinate variation $X_{k+1} - X_k$ of a non-defective container is calculated. Then, the maximum value (max (a, b) described later) and the minimum value (min (a, b) described later) which provide the above described allowable range are respectively stored in the maximum value table TB1 and the minimum value table TB2 each shown in FIG. 6 as allowable value tables TB. In this case, the value k is 0j or 1j.

In FIG. 5, since images are not stable at a several lines near the top and the valley, they must be excluded or assigned a large allowable value. Therefore, the allowable value of $X_{K+1} - X_K$ is determined as follows based on the coordinate variation of a non-defective container.

$$\min(a,b) - \alpha < X_{k+1} - X_k < \max(a,b) + \alpha$$

where max(a,b) means the maximum value "a" or "b" (shown below) whichever is larger. Likewise, min(a,b) means the minimum value "a" or "b" whichever is smaller.

$$a = X_k - X_{k-1}$$

$$b = X_{k+b} - X_{k+1}$$

$\alpha$ is a fixed value for moderating a detected sensitivity in consideration of a quantization error, etc. generated when an image is converted to a digital image.

"a" and "b" can also be assigned to determine the allowable range of two lines as follows.

$$a = X_{k-1} - X_{k-2}$$

$$b = X_{k+3} - X_{k+2}$$

Figure 6:
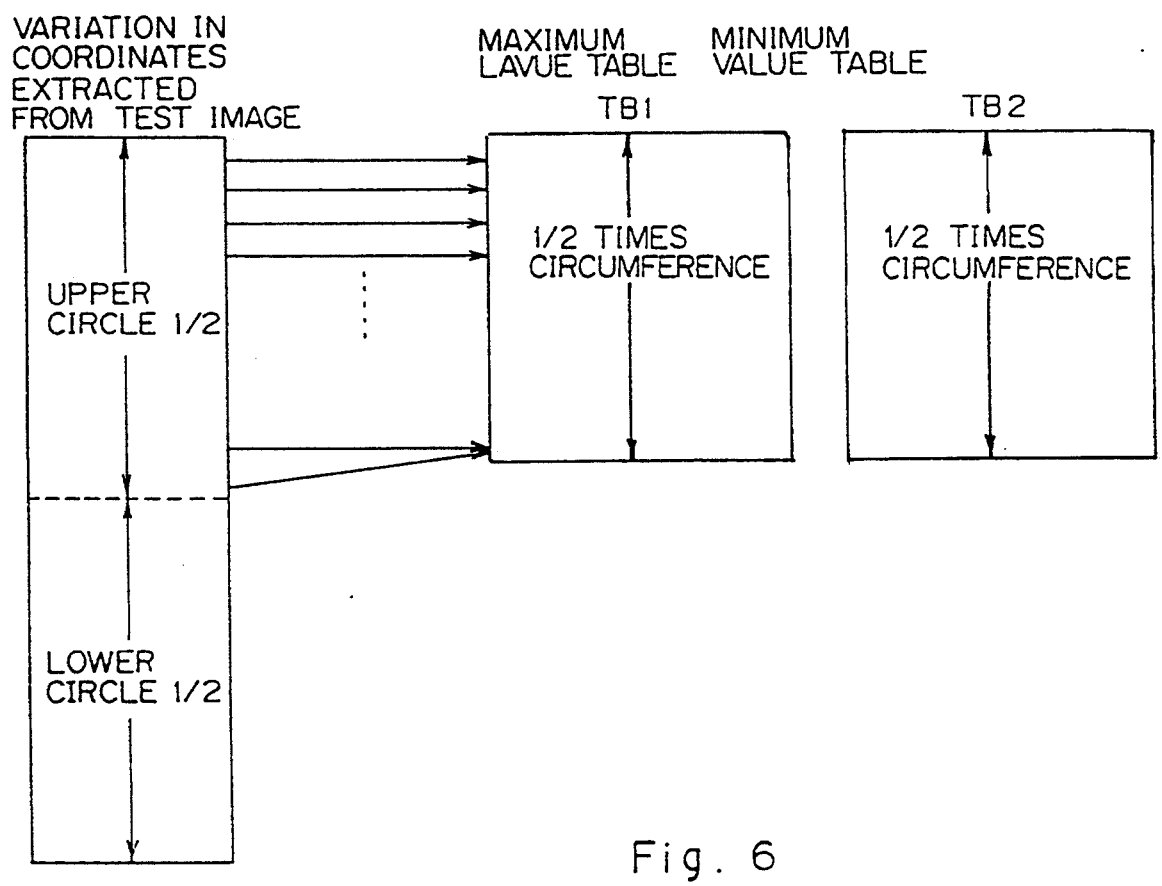
FIG. 6 is a block diagram for explaining the determination of the circularity.

Thus, the highlighted portion determining circuit 11 stores an allowable value of a non-defective container for each line as a maximum table TB1 and a minimum table TB2 shown in FIG. 6, and serially compares for a circularity test the variation in coordinates of a test image with the allowable value indicated in the table TB1 or TB2.

If a predetermined number of scanning lines of a non-defective container does not match the number of scanning lines of a test image, the above described comparison is performed serially from the top or the valley of the container to its center. The difference in the number of scanning lines is balanced around the center where the variation is smaller than in upper or lower lines. That is, when the number of lines shown in the allowable table of a non-defective container is smaller, the comparison is performed using the allowable value for the center line (refer to FIG. 6). In FIG. 6, the same process is performed twice for an upper circle and a lower circle, and the allowable value table stores the values only for half a circle.

Figure 7A:
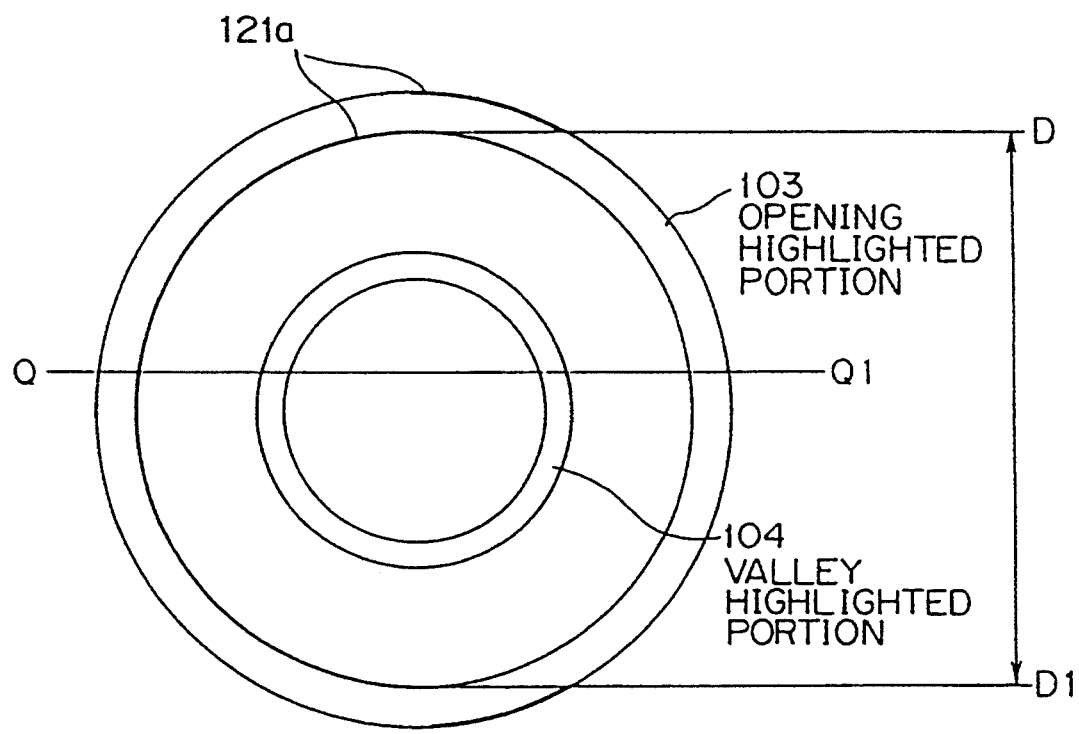
FIGS. 7A and 7B show how to detect a point in all inner circumference of a highlighted portion.
Figure 7B:
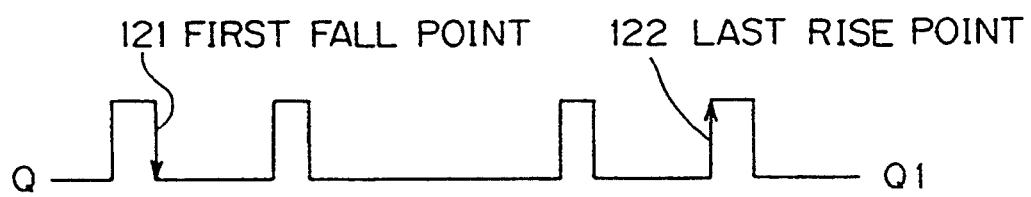

The above described test is performed for an outer circumference. The test method for an inner circumference is explained below. FIG. 7 shows how to detect coordinates in an inner circumference of a highlighted portion. FIG. 7A is a plan view of a test container; and FIG. 7B shows in binary how continuous tone image signals change at the highlighted portions in the scanning line Q-Q1. First fall points of binary signals 121 in scanning lines shown in FIG. 7B detect the coordinates 121a indicated as the bold curves shown in FIG. 7A. Since the coordinates in the inner circumference range between D and D1, the line D-D1 is determined to be the line where the coordinate variation shows inversion, thereby obtaining the coordinates of the left half inner circle. Likewise, each of the last rise points 122 in each scanning line generates the right half inner circle. Thus, the circularity test is performed on the inner circumference.

Figure 8:
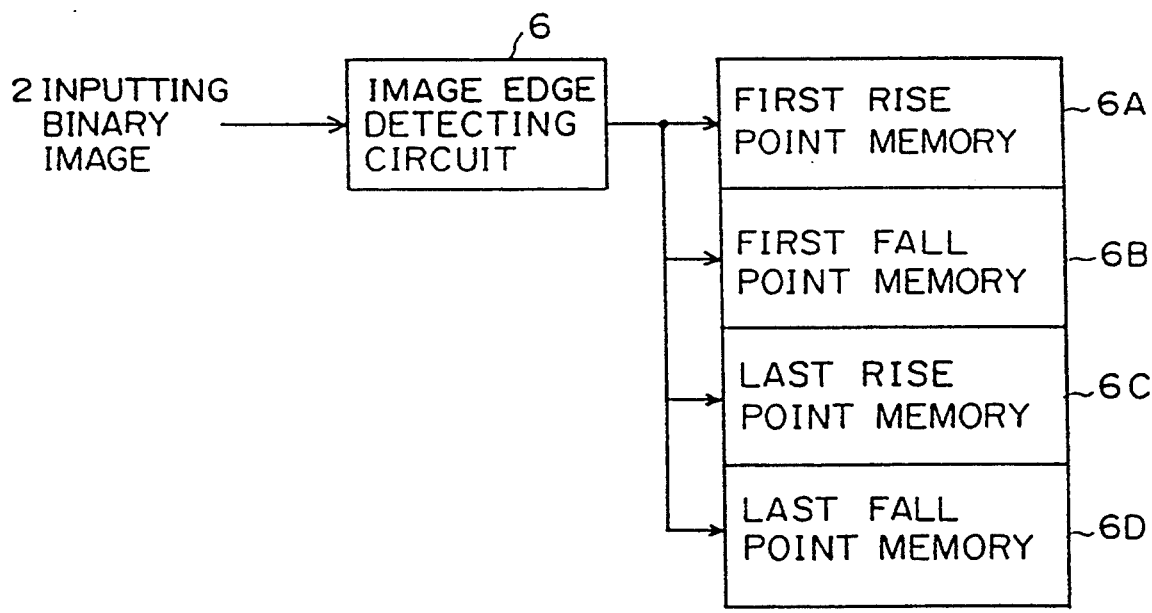
FIG. 8 is a block diagram of the detailed configuration of the image edge detecting circuit.

FIG. 8 shows the further detailed configuration of the image edge detecting circuit 6 shown in FIG. 1. In FIG. 8, a memory 6A stores a first rise point; a memory 6B sores a first fall point; a memory 6C stores a last rise point; and a memory 6D stores a last fall point. The data in the memories 6A and 6D enable an outer circumference to be detected, and the data in the memories 6B and 6C enables an inner circumference to be detected.

Figure 3:
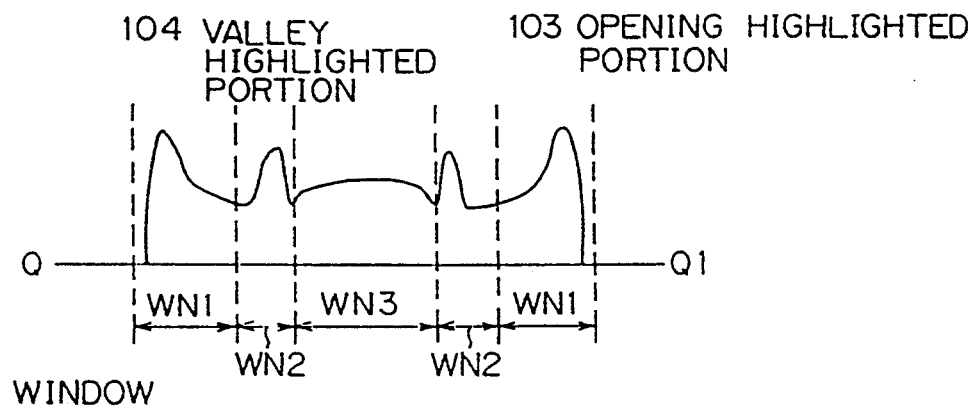
FIG. 3 shows the relationship between the intensity variations inside a cylindrical container and the division of a window based on the present invention.

The deformation and a concave on a container, and dust attracted to it can be detected with a high defect-detection precision when the above described outer circumference is tested in a circularity test on the highlighted portions. Therefore, the number of windows can be reduced by concurrently detecting black and white spots through the circularity test and the conventional defect detecting circuit. FIG. corresponds to FIG. 13B, and shows an embodiment of a window based on the present invention. That is, in FIG. 3, a new window WN1 is generated by combining a window W1 including the highlighted opening portion 103 shown in FIG. 13 and the adjacent window W2. Likewise, a new window WN2 is generated by combining a window W4 including the highlighted valley portion 104 shown in FIG. 13 and the adjacent window Another new window WN3 corresponds to a window W5 for the central part of the valley shown in FIG. Thus, there are three window areas WN1, WN2, and WN3, thereby decreasing the number of areas.

Figure 9:
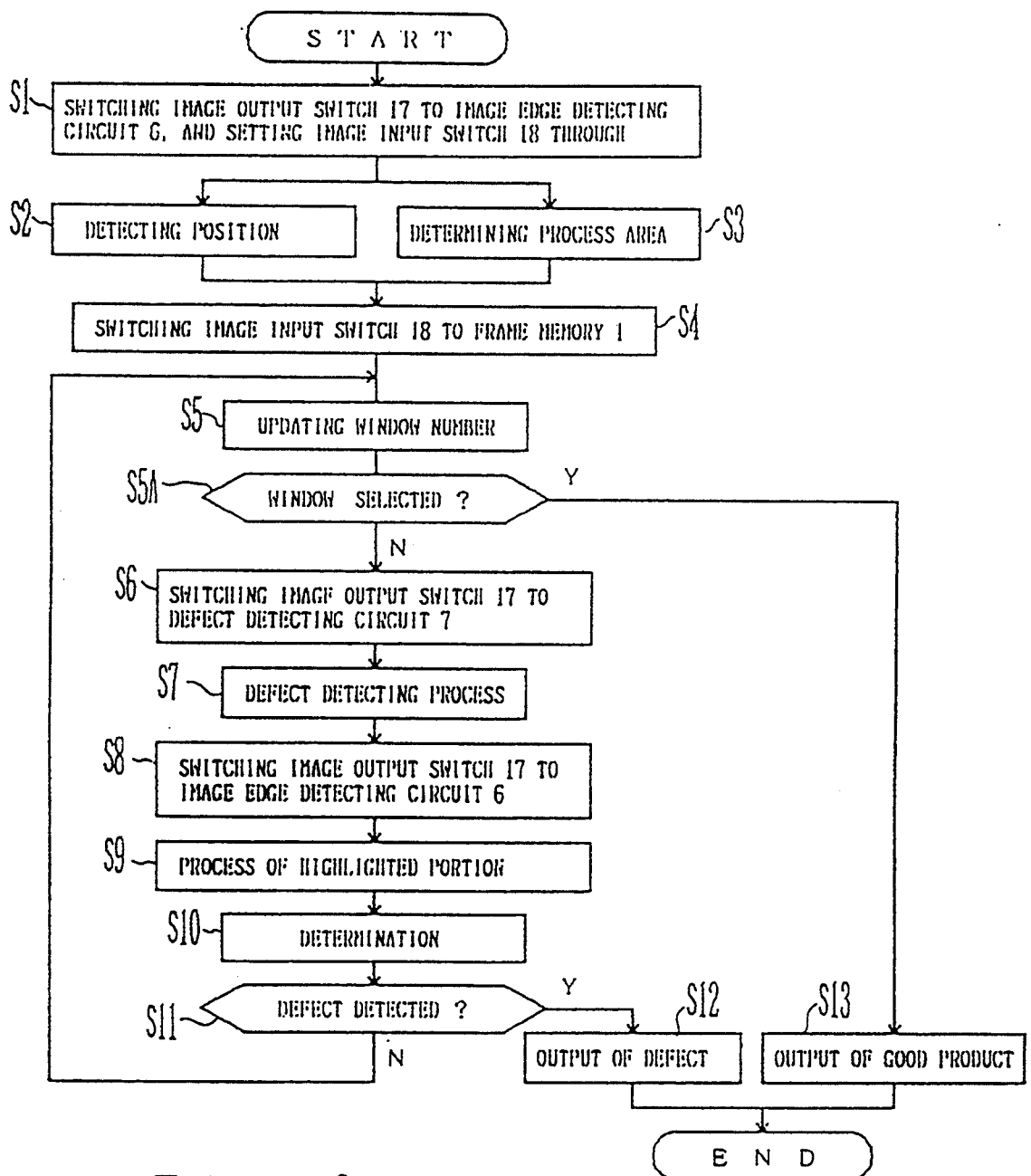
FIG. 9 is a flowchart for explaining the procedure of the operation associated with the configuration shown in FIG. 1.

FIG. 9 is a flowchart indicating the procedure of the operation shown in FIG. 1. The operation is explained by referring to FIG. 9. Numbers S1–S13 indicate the step numbers shown in FIG. 9. First, the image output switch 17 is switched to the image edge detecting circuit 6. Simultaneously, the image input switch 18 is put through, that is, switched to directly input a multi-value image signal PO (S1). Thus, the difference in the position of a target image is detected ($2). Simultaneously, a process area is determined through the X projection circuit 9, the Y projection circuit 10, and the process area determining circuit 14 ($3).

That is, in step S 2, the position difference amounts αx and Δy of a container image are obtained through the position difference amount determining circuit 13, and a value for correcting a horizontal position difference is sent to the image address generating circuit 3 so that a window can be generated at the right position. In step S 3, a container image is isolated from another if they are arranged adjacent to each other by the process area determining circuit 14 so that one scanning area does not contain adjacent container images.

Then, the image input switch 18 is switched to the frame memory 1 ($4), and the following acceptability determining process is performed based on the continuous tone image data 1a in the frame memory 1. First, a test window area of a test can refers to the area of the window WN1 including the highlighted opening portion 103 and masks other window areas WN2 and WN3 ($5). Next, the process in step S6 is performed until the test is completed for all the windows (branch to N in step S5A). In step S 6, the image output switch 17 is switched to the defect detecting circuit 7 to detect a defect through the defect detecting circuit 7 and the defect detection determining circuit 12 (S7). The defect detecting circuit 7 detects black or white spots by the differentiation method, etc. to count the number of picture elements indicating a defect. The defect detection determining circuit 12 compares the counted number of picture elements indicating a defect with a predetermined value to determine the acceptability and output the result to the final determining circuit 15 in the step described later.

Then, the image output switch 17 is switched to the image edge detecting circuit 6 to operate the image edge detecting circuit 6 again, represent highlighted portion in binary as described above so that coordinates or an area of an outer or inner circle can be calculated ($9), perform the circularity test and compare the results with the standard area value through the highlighted portion determining circuit 11 so that the acceptability can be determined, and output the determination result to the final determining circuit 15 in the step described later.

The final determining circuit 15 instructs the output circuit 16 to output a defect (S12) if either the highlighted portion determining circuit 11 or the defect detection determining circuit 12 determines a defect (S10 to S11, branch to Y). If the test container is determined to be a non-defective product in step S 11, control is returned to step S 5 again, the next test area is the window area WN2 containing the highlighted valley portion 104, the other areas WN1 and WN3 are masked, and the following steps up to step 12 are repeated. When the tests on all the windows are completed up to the window WN3 (in step SSA, branch to Y), the output circuit 16 is instructed to output the non-defective product through the final determining circuit 15 (S13).

Figure 2:
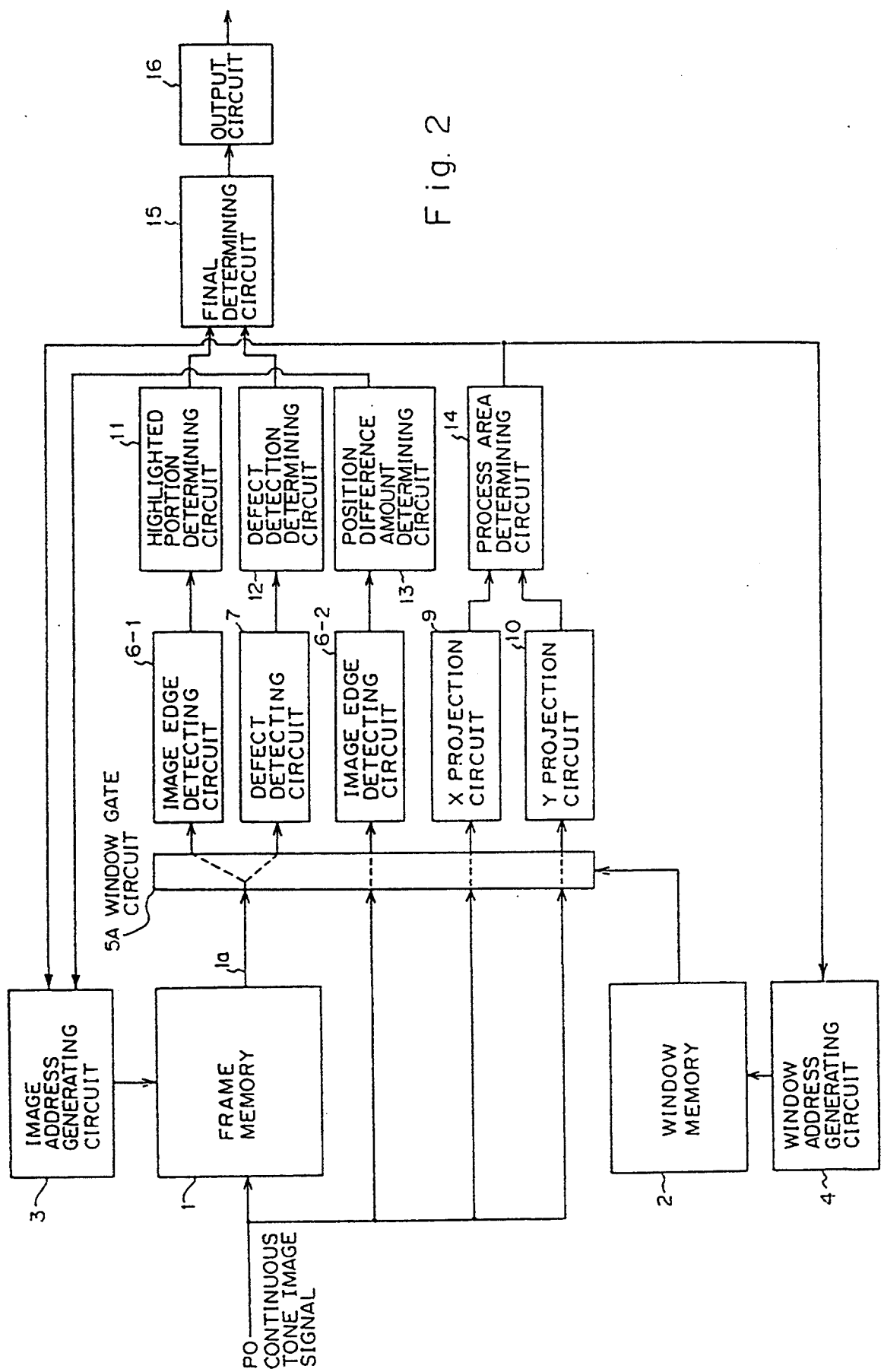
FIG. 2 is a block diagram of the hardware configuration of the second embodiment of the present invention.

FIG. 2 shows the block circuit in which the process shown in FIG. 1 can be performed in a high speed. In FIG. 2, the image input switch 18 shown in FIG. 1 is omitted and the window circuit 5 is revised as a new window circuit DA, two circuits 6-1 and 6-2 corresponding to the image edge detecting circuit 6 are provided where one image edge detecting circuit 6-2 directly receives a multi-value image signal PO (through the window gate circuit 5A) and provides the detection result for the position difference amount determining circuit Furthermore, the image output switch 17 shown in FIG. 1 is omitted and the output image signal 1a from the frame memory is provided concurrently for the other image edge detecting circuit 6-1 and the defect detecting circuit 7 (through the window gate circuit 5A) to concurrently perform the processes by the highlighted portion determining circuit and the defect detecting circuit 11.

Figure 10:
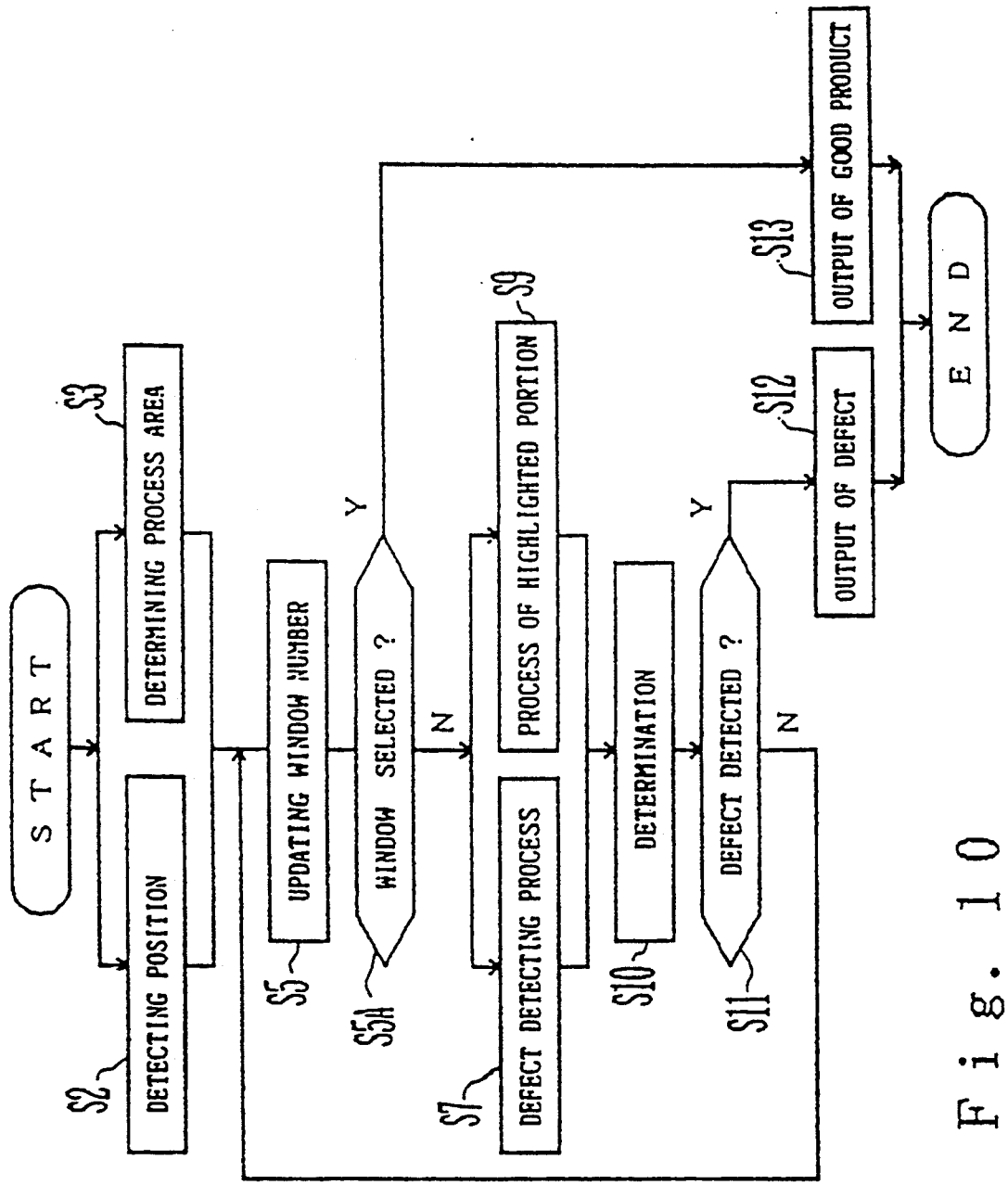
FIG. 10 is a flowchart for explaining the procedure of the operation associated with the configuration shown in FIG. 2.

FIG. 10 is a flowchart for describing the procedure of the operation shown in FIG. 2, where the switching steps S 1, S 4, S 0, and S 8 of the switches 17 and 18 are omitted from the procedure shown in FIG. 9. Additionally, the defect detecting process in step S 7 and the process of highlighted portions in step S 9 are performed concurrently.

Figure 11A:
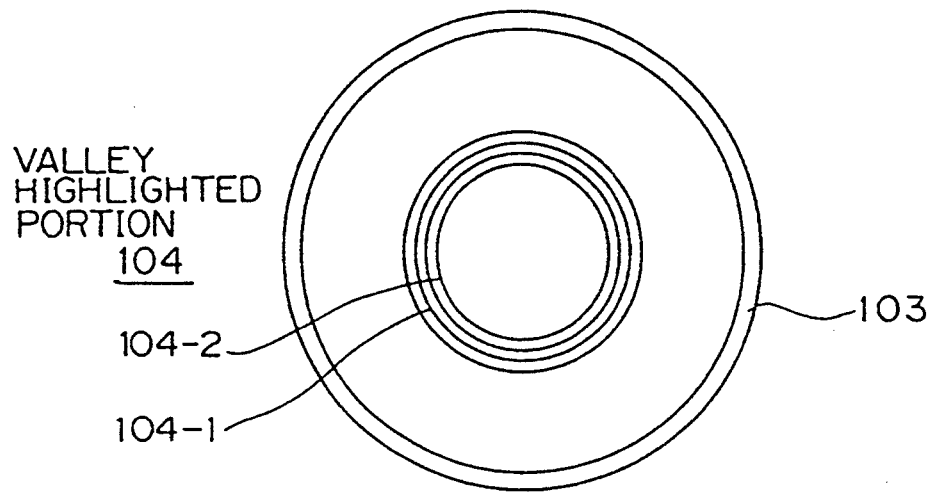
FIGS. 11A and 11B show the highlighted portion inside a container having an unusual valley shape.
Figure 11B:
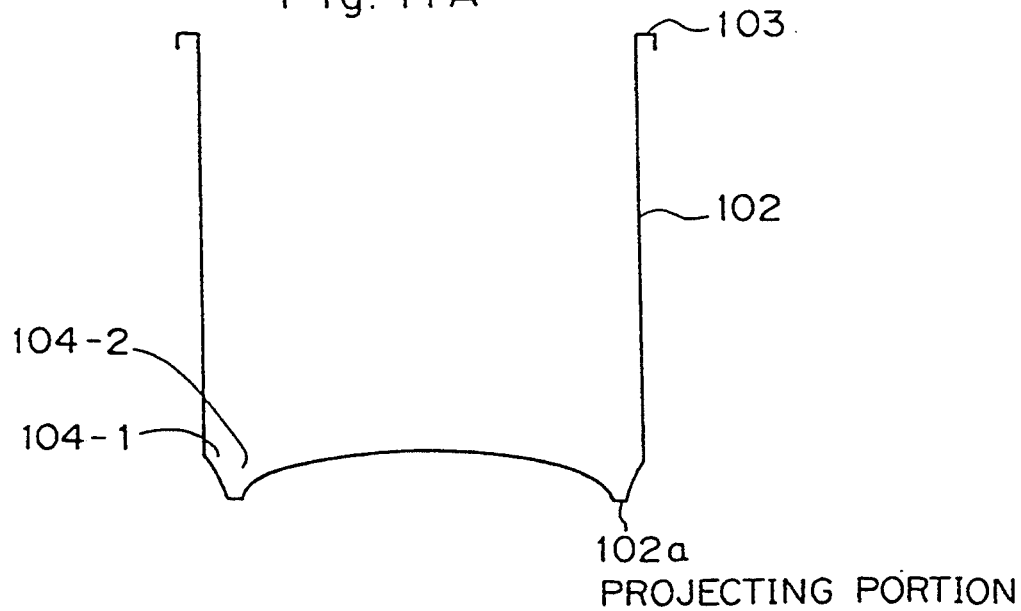

FIG. 11 is an explanatory view of a highlighted valley portion of a container whose valley is formed uniquely. FIG. 11A is a plan view (image); and FIG. 11B is a sectional view. In this embodiment, the highlighted valley portion 104 is generated as 104-1 and 104-2. In this way, a highlighted valley portion can be generated concentrically in more than one circle depending on the shape of the valley part of a container. In this case, the valley area is appropriately divided and the number of windows is increased correspondingly. Step S 5 shown in FIGS. 9 and 10 shows a conditional branch involved. Since a valley portion is a comparatively small area to be scanned, it can be processed at a high speed even though the number of windows is increased to some extent.

Figure 14:
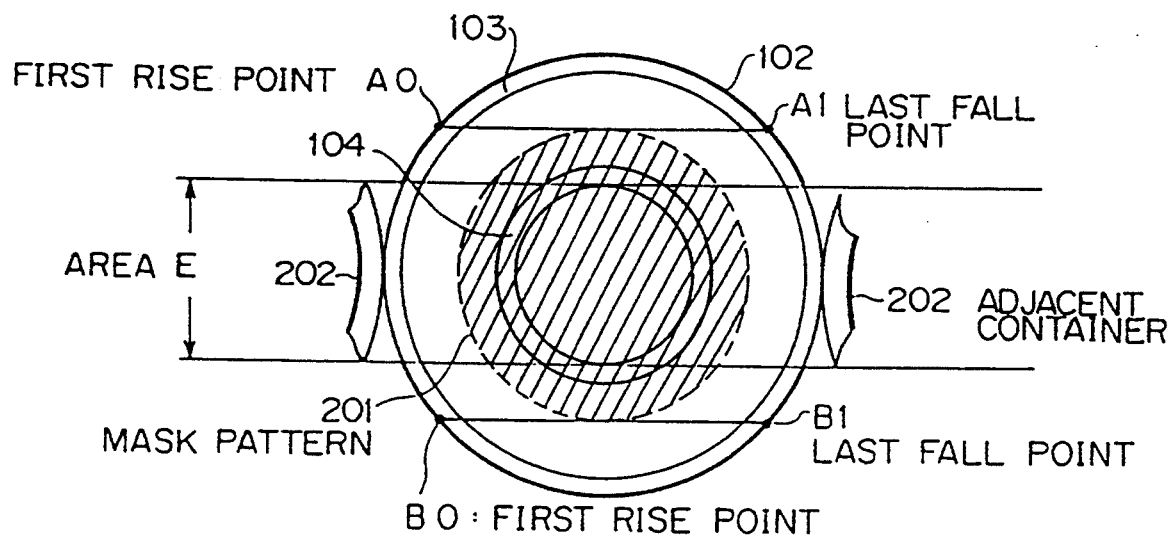
FIG. 14 shows how to detect the position of a target image in the first embodiment.

Additional explanation about an embodiment of a position detecting operation performed for a test image by the image edge detecting circuit 6 (FIG. 1) is given below by referring to FIGS. 14 and 17. FIG. 14 shows an image of a highlighted portion converted to the binary representation by the image edge detecting circuit 6. In FIG. 14, 201 is a mask pattern, and 201-2 is a container adjacent to a test container 201 (102-1). That is, the highlighted valley portion 104 is masked by the mask pattern 201 through the window gate circuit 5 shown in FIG. 1. The coordinates indicated by the bold curves shown in FIG. 14 can be obtained when first rise points such as A0 and B0 and last fall points such as A1 and B1 are detected in the scanning direction in a binary image. However, incorrect coordinates are obtained in the area E when any container is adjacent to the test container. Therefore, the position of the test container must be detected by the lines near the longest possible lines such as A0–A1 and B0–B1 in the horizontal scanning lines connecting the above described coordinates indicated by the bold curves out of the area E.

Figure 15:
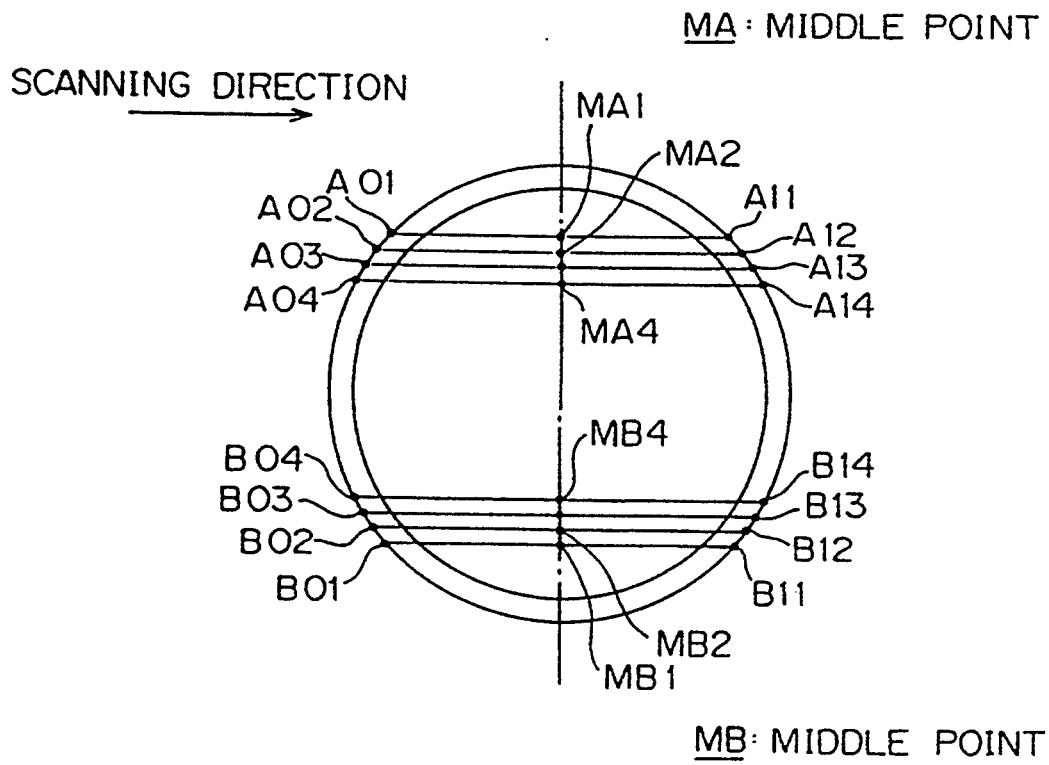
FIG. 15 shows the detailed drawing for supplementing FIG. 14.

FIG. 15 shows how the center positions (x coordinates) along horizontal scanning lines of a test container are obtained by calculating middle points MA (MA1 ... MA4) of lines A01–A11 ..... A04–A14 near the lines A0–A1 and B0–B1 out of the area E as described above by referring to FIG. 14, likewise by calculating the middle points MB (MB1 ... MB4) of lines B01–B11, ..., B04–B14, and by calculating the average value of these middle points MA1 ... MA4 and MB1 ... MB4.

The Y coordinates can be obtained by calculating the average value of the coordinates of both ends (upper and lower limits) of the X direction projected pattern obtained by the X projection circuit 9 shown in FIG. 1.

Figure 16:
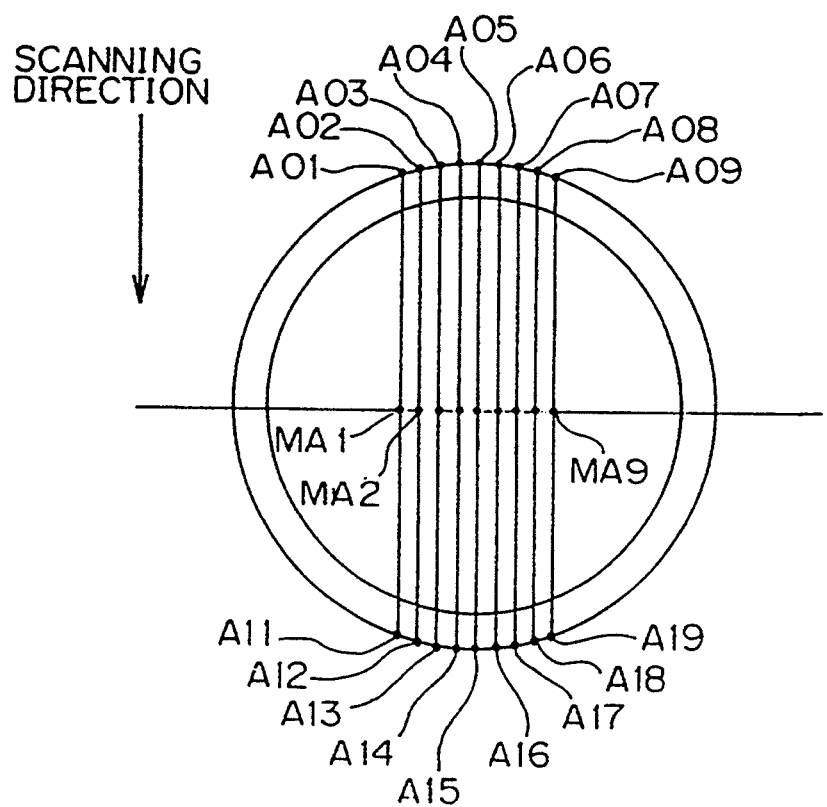
FIG. 16 shows how to detect a target image in the second embodiment of the present invention.

FIG. 16 shows an example of a position detection by the method similar to the above described method in which an image is scanned vertically (in the Y direction) after the image is inputted to the frame memory 1a. That is, if containers are conveyed horizontally (in the X direction), they are not adjacent to one another vertically (in the Y direction). Therefore, there is no need to consider the area E shown in FIG. 14.

In FIG. 15, a multi-value continuous tone image signal PO can be used directly. However, in FIG. 16, an image signal 1a must be used from the frame memory 1, thereby causing delay and incorrect position detection of a target image. However, the delay can be minimized by limiting the scanning operation shown in FIG. 16 to a local area.

Figure 17A:
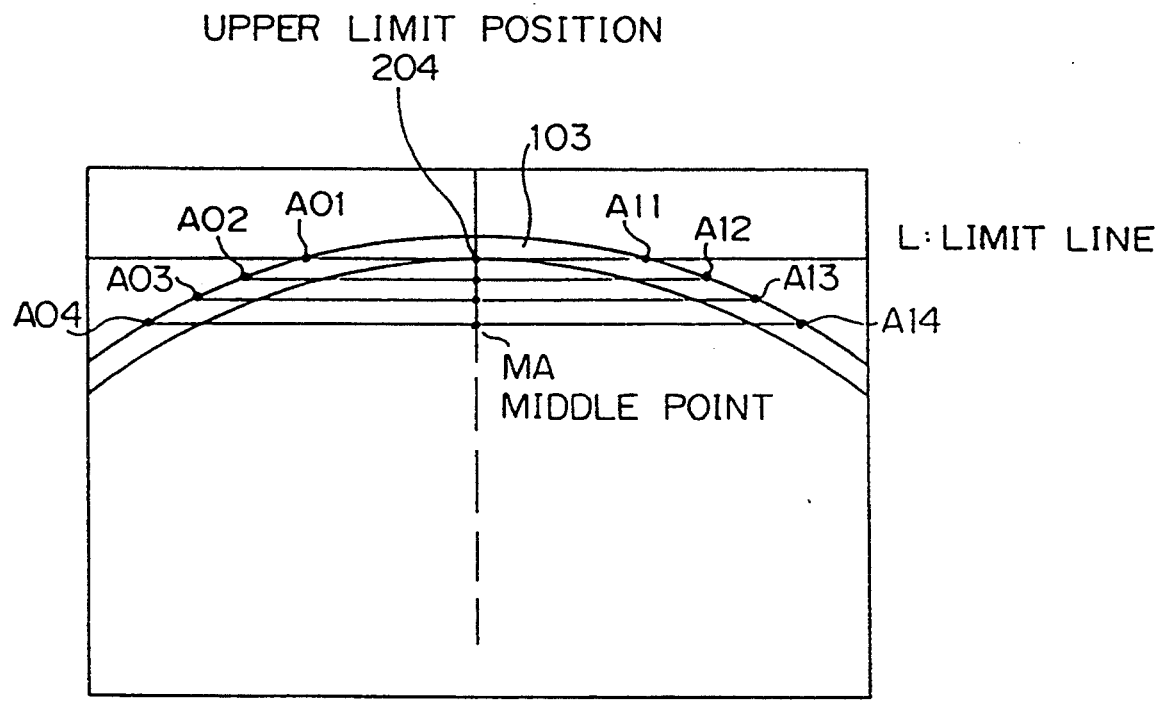
FIGS. 17A and 17B show how to detect a target image in the third embodiment of the present invention.
Figure 17B:
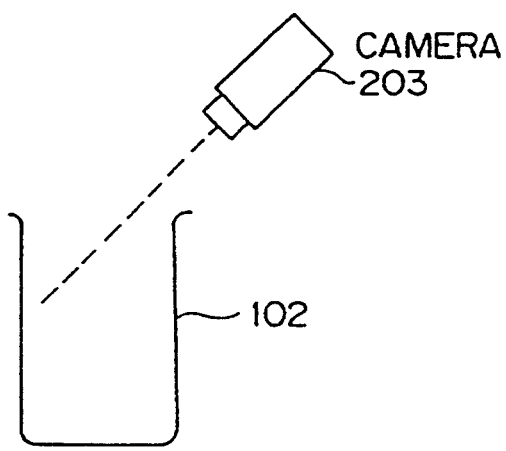

FIG. 17 shows another example of detecting the position of a container by regarding highlighted portions. This example is captured by a camera 203 as an oblique top view of the container 102. The highlighted opening portion 103 is observed as a binary image as shown in FIG. 17A. In this detected image, first rise points A01 ... A04 and last fall points A11 ... A14 are obtained in each horizontal scanning line. Then, an average value MA of the middle points of lines A01-A11 ...., and A04–A14 are calculated to specify the horizontal position of the test container. The vertical position of the test container can be specified by obtaining the limit line L at which the length of the horizontal scanning line falls below a predetermined value, thereby specifying the upper limit of the horizontal position of the test container.

This position detecting method can be applied when the upper limit of a container is specified as a predetermined position determination point.

Figure 18A:
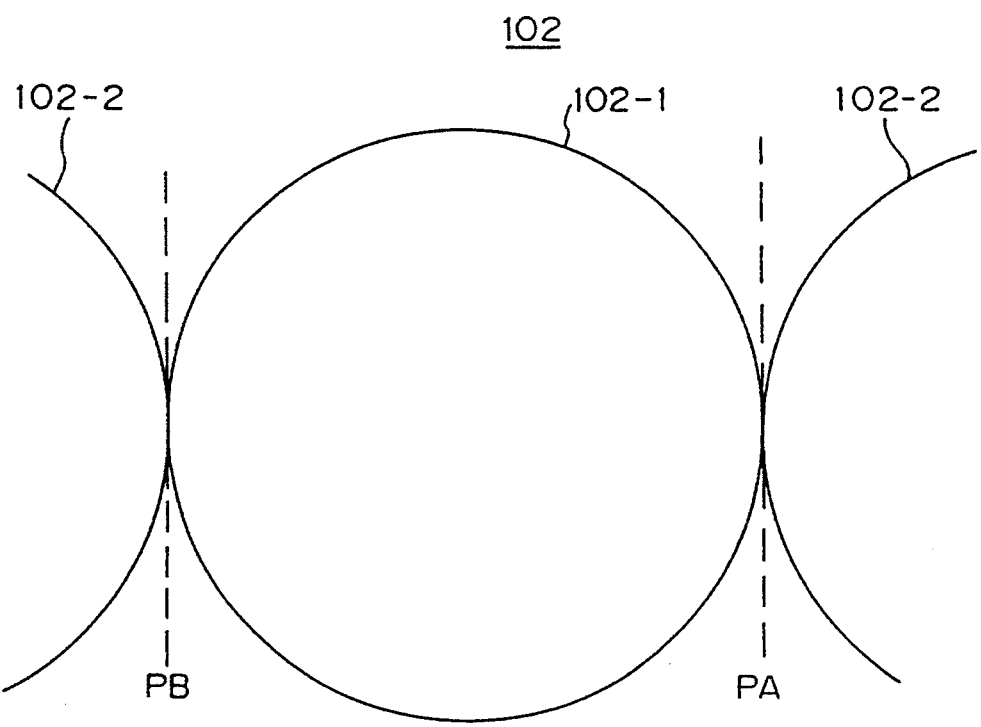
FIGS. 18A and 18B show the conventional method of detecting a container adjacent point.

Additional explanation is given below, by referring to FIGS. 18 and 21, about an embodiment of a process area determining operation when a test container is adjacent to other containers. The process area determining circuit 14 shown in FIG. 1 performs an arithmetic operation of determining a process area according to the information from the X projection circuit 9 and the Y projection circuit 10. FIG. 18 shows the conventional method of determining a process area. FIG. 18A shows a binary image converted to the binary representation of the whole container based on a threshold, where 102-1 is a test container; and 102-2 is a container adjacent to the test container 102-1. In this case, the containers are horizontally adjacent to one another.

Figure 18B:
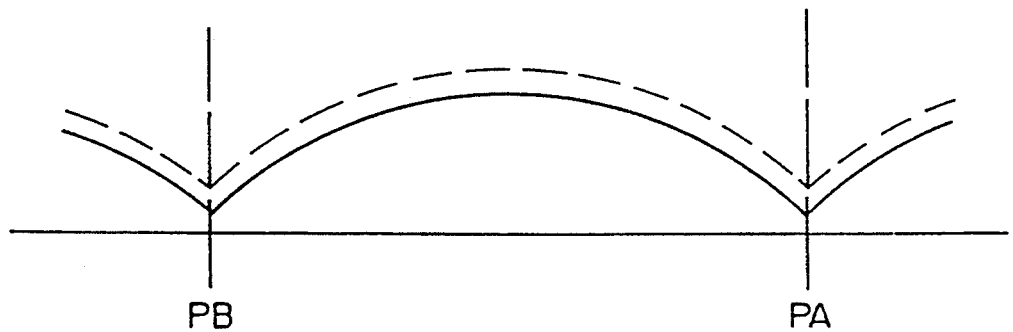
Figure 18C:
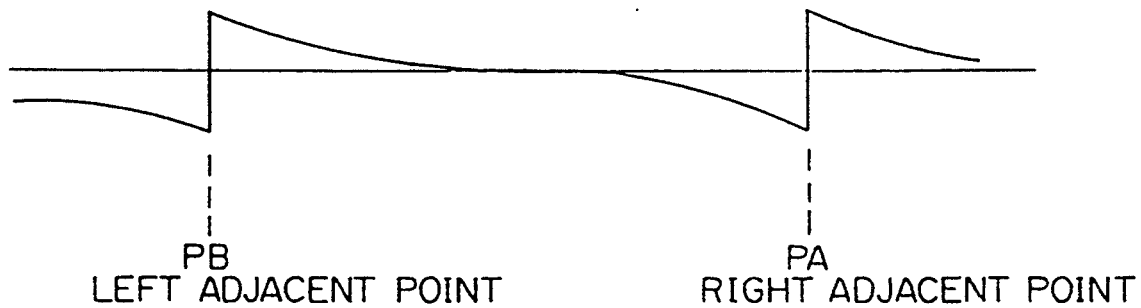

FIG. 18B shows the number of projected picture elements of the image shown in FIG. 18A calculated in the vertical direction. FIG. 18C shows the difference obtained by subtracting the projected amount (the number of projected picture elements). a relatively simple pattern shown in FIG. 18, a right adjacent point PA and a left adjacent point PB can be detected by a change point shown in FIG. 18C, thereby isolating the adjacent containers.

Figure 19A:
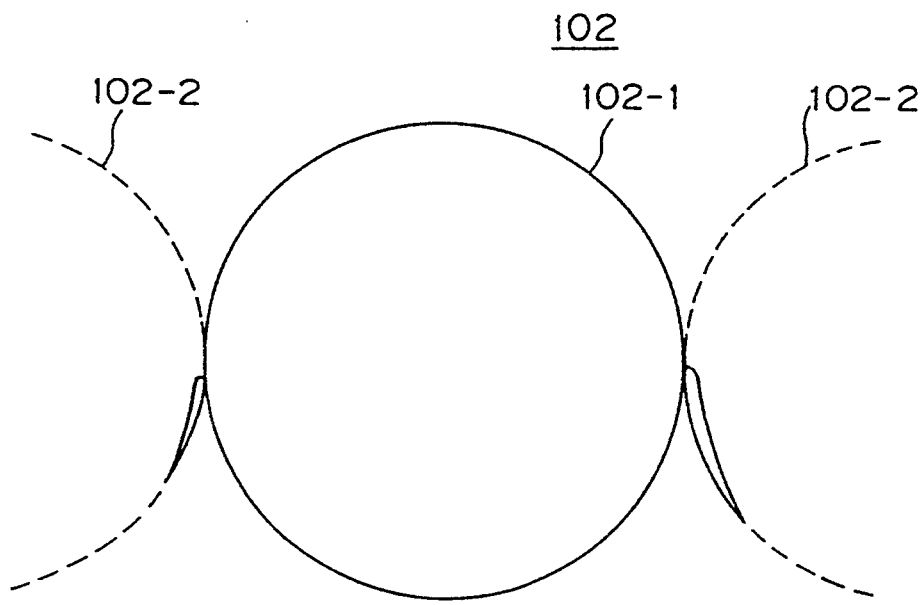
FIGS. 19A and 19B show an example where an adjacent point cannot be detected in the method shown in FIG. 18.
Figure 19B:
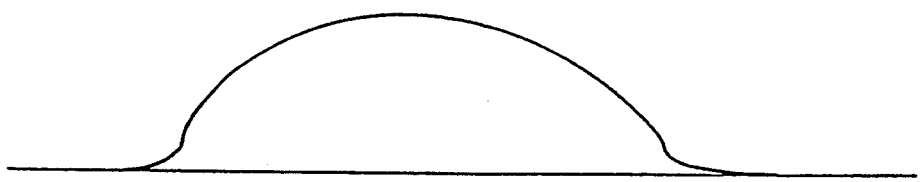
Figure 19C:
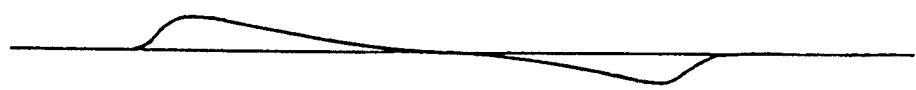

FIG. 19 is a view for explaining the conventional method similar to one shown in FIG. 18 in which adjacent points cannot be detected easily. That is, as shown by the actual test image in FIG. 19A, only a part of adjacent containers may be detected in binary. Therefore, the projection pattern comes out as shown in FIG. 19B, and the difference projection pattern is represented as shown in FIG. 19C, thereby preventing the containers from being isolated easily.

FIG. 20 is a view for explaining the process area determining method based on the present invention for testing a container adjacent to other ones. That is, a threshold is determined to detect by the Y projection circuit 10 a highlighted opening portion 103 as a ring-shaped image, a multi-value continuous tone image signal PO is converted to the binary representation to obtain a binary image shown in FIG. 20A, and then a projection pattern of this binary image shown in FIG. 20B can be obtained by calculating the projection in the Y direction vertical to the adjacent direction (horizontally, that is, the X direction).

Next, the process area determining circuit 14 calculates the difference in the projected amount (the number of projected picture elements) shown in FIG. 20B from the center to the opening of a test container 102-1 as shown by the arrow 301 in FIG. 20C, and obtains a difference projection pattern as shown in FIG. 20C. Then, adjacent points can be obtained as follows.

That is, to obtain the right adjacent point PA, a detecting operation is performed from a side point P1 to the opening portion shown in FIG. 20C to obtain the point $\Delta PM$ at which the maximum difference projected amount is obtained (maximum difference projection point) within the range to the point PD at which the difference projection pattern graph first indicates a turn to decrease (difference decrease start point).

FIG. 21 is a view enlarged around the point $\Delta PM$. In FIG. 21, PM marks the maximum projected amount in the highlighted opening portion 103 (referred to as the maximum projection point). $\Delta PM$ is a point near the maximum projection point PM and can be obtained as follows relative to the maximum projection point PM, That is, the picture element number k is sequentially assigned from the center of the test container 102 to the X direction. The number of projected picture elements is Tk at the position of the picture element number k. The difference between the Tk and the number of the projected picture elements $T_{k+4}$ at the point four picture elements apart to the right can be obtained as follows.

$$\Delta T_k = T_{k+4} - T_k$$

If thus calculated differences generate a difference projection pattern, $\Delta PM$ indicating the maximum value of $\Delta T_k$ is determined to be the point four picture elements inside the maximum projection point PM.

In the present invention, the right adjacent point PA can be obtained by adding a predetermined correction value $\beta$ to the maximum difference projection point $\Delta$PM. According to the result, adjacent containers are isolated and the resultant coordinates determine a process area.

The maximum difference projection point $\Delta$PM is obtained first because it can be detected as stable coordinates while the maximum projection point PM is subject to the influence of the fluctuation of the ring width of the highlighted opening portion 103 caused by the intensity of the illumination applied to the test container.

Thus, the present invention can reduce the influence of adjacent containers by detecting an adjacent point from the center to the opening of a test container by regarding the highlighted opening portions 103.

Figure 23:
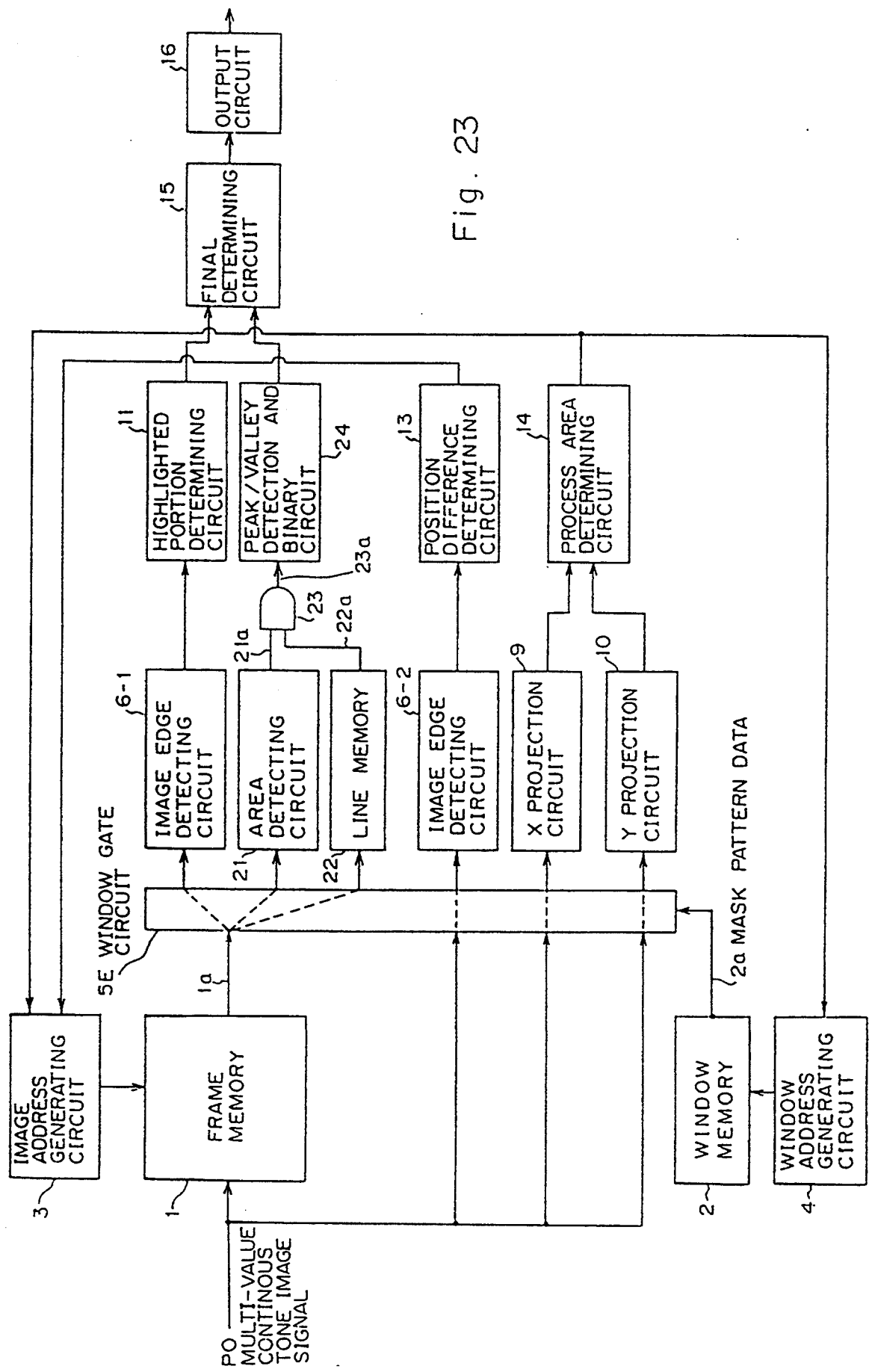
FIG. 23 is a block diagram for explaining the hardware configuration of the third embodiment of the present invention.

Another embodiment of the present invention is described below by referring to FIGS. 22 through 28. FIG. 23 is a block diagram of a hardware as an embodiment of the present invention. In FIG. 23, a multi-value (8 bits, for example) continuous tone image signal PO is obtained by AD-converting the video signal provided by raster-scanning the surface of a TV camera not shown in FIG. 23. A frame memory 1 receives a multi-value continuous tone image signal PO to store them as multi-value image data; an address generating circuit 3 is provided for the frame memory; a window memory 2 stores a mask pattern for each window; an address circuit 4 is provided for the window memory; a window gate 5E masks with a mask pattern data 2a obtained from the window memory 2 a multi-value continuous tone image signal PO or an image signal la read from the frame memory 1, and passes only the image signal PO or the image signal 1a for the specified window area.

Image edge detecting circuits 6-1 and 6-2 detect the edge of an image, that is, the outer edge (the point in the outer circumference) and the inner edge (the point in the inner circumference) of a ring-shaped highlighted portion. In this case, an inputted image signal is converted to the binary representation using a predetermined threshold used for detecting the position of a target image or performing the circularity test. Then, the image edge detecting circuit 6-1 and 6-2 store the rise point and the fall point coordinates of the binary signals each indicating the edge of an image in their own memories. A circuit 11 performs the circularity test on the coordinates of the points in the outer and inner circumferences detected by the image edge detecting circuit 6-1.

A circuit 13 detects the difference between the center position of an actual target image detected by the image edge detecting circuit 6-2 by applying the latest multi-value continuous tone image signal PO and the central position of a predetermined window.

An area detecting circuit 21 receives a multi-value continuous tone signal la through the frame memory 1 and the window gate circuit 5E, and outputs an area signal 21a as a signal for specifying an area to be scanned (that is, an area within the contour of a test container) for a defect on each of the horizontal scanning lines for the purpose of detecting an image indicating a defect.

A line memory 22 receives an image signal la for each of the horizontal scanning lines in synchronous with the area detecting circuit 21, and temporarily stores it.

An AND gate 23 ANDs an area signal 21a and a continuous tone image signal 22a outputted by the line memory 22 as an image signal for each of the horizontal scanning lines corresponding to an area signal 21a, and outputs a continuous tone image signal for an area to be searched for a defect (referred to as a test area continuous tone image signal).

A peak/valley detection and binary-conversion circuit 24 is an important part of the present invention and detects from an image signal 23a a picture element indicating a defect including a defective peak/valley described by referring to FIG. 22.

An X projection circuit 9 obtains an X-direction projection pattern of a target image using a multi-value image signal PO which has passed through the window gate circuit 5E. Likewise, a Y projection circuit 10 obtains a Y-direction projection pattern of a target image. A process area determining circuit 14 determines using these output data of the projection circuits 9 and 10 the area of a test container image not adjacent to other container images.

A final determining circuit 15 receives a determination result from the peak/valley detection and binary-conversion circuit 24 to make final determination; and an output circuit 16 outputs the acceptability according to a determination signal outputted by the final determining circuit 15.

In the present invention, the area detecting circuit 21 detects the contour of a container as a test area, and the area is searched for a defect according to the equations (1), (2), (1A), and (2A) shown in FIGS. 22A and 22B.

Additional information about the multi-value continuous tone image signal PO is described below. That is, an analog video signal obtained by raster-scanning the image taken by a TV camera can be converted to a digital signal using an A/D converting circuit, etc. by a common method. Then, the multi-value continuous tone image signal PO is a digital signal converted by the A/D converting circuit, etc.

Figure 31A:
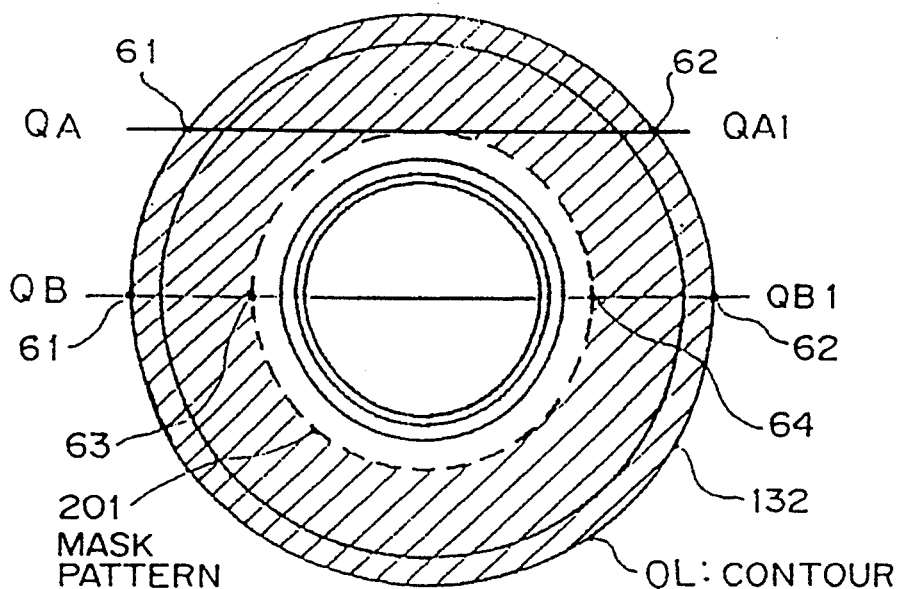
FIGS. 31A, 31B, and 31C are views for explaining the operation of the area detecting circuit.
Figure 31B:
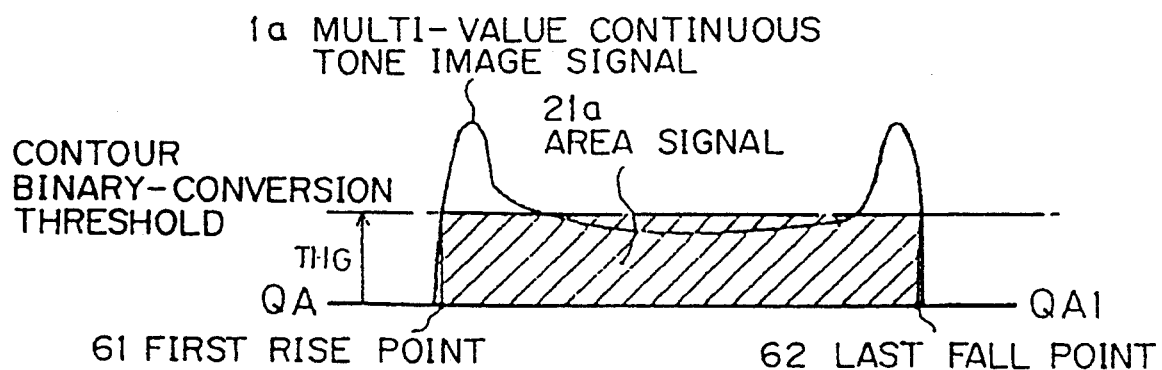
Figure 31C:
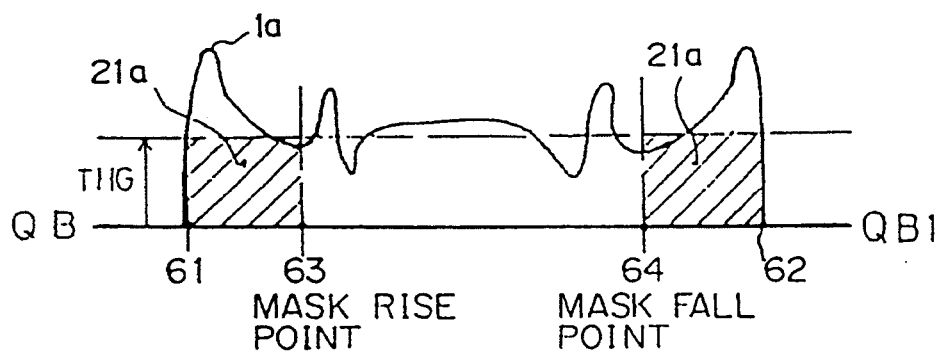

FIGS. 31A through 31C show the operation of the above described area detecting circuit 21, that is, the operation for detecting the test area (namely, the contour of a container). That is, FIG. 31A is a top view of the container 132, where OL shows the contour, the lines QA-QA1 and QB-QB1 show scanning lines (or section), and 201 is a mask pattern. FIG. indicates the relationship between the intensity variations (continuous tone image signal) along the section QA-QA1 and the area to be tested. FIG. 31C shows the relationship between the intensity variations (continuous tone image signal) along the section QB-QB1 and the test area.

As described above, the area detecting circuit 21 receives a multi-value continuous tone image signal 1a from the frame memory I through the window gate circuit 5E, and converts it to a binary number using a threshold THG (referred to as a binary contour threshold for convenience) as shown in FIG. 31B. Then, the first rise point 61 and the last fall point 62 of the binary signal are detected, and the range between the these points is defined as a process range.

A signal indicating the process range, that is, the signal indicating "1" for the diagonal-shaded portion shown in FIG. 31B is outputted as the area signal 21a. The area signal 21a and the continuous tone signal 22a for 1 scanning line temporarily stored by the line memory 22 corresponding to the area signal 21a are ANDed through the AND gate 23 for outputting the above described continuous tone signal 23a for the test area.

Alternatively, the area signal 21a can be obtained from the window signal obtained from the mask pattern data 2a from the window memory 2 (that is, a signal indicating the area excluding the mask pattern area), or as a combination of the area signal 21a and the window signal.

The area between the points 63 and 04 shown in FIG. 31C corresponds to the area of the mask pattern 201 shown in FIG. 31A, where 63 is a mask rise point, and 64 is a mask fall point. In this example, the mask pattern 201 masks the area in which the variation of the continuous tone image signal 1a of the container valley is anticipated to be somewhat complicated.

In this case, the window signal can be obtained as "1" in the area excluding the area between the points 63 and 64 in the mask area. The signal obtained by combining the original area signal indicating "1" only between the first rise point 61 and the last fall point and the window signal, that is, the signal indicating "1" only in the diagonal-shaded portion between the points 61 and 63 and between the points 64 and 62 shown in FIG. 31C is the area signal 21a finally outputted from the area detecting circuit 21.

The test area indicated by diagonal shaped portion as shown in FIG. 31C can be assigned the optimum number $\alpha$ of picture elements and the threshold THD in equations (1), (2), (1A), and (2A) shown in FIGS. 22A and 22B.

Thus, the optimum number $\alpha$ of picture elements according to the optical characteristics of the inner surface of a container and the threshold THD are selected by concentrically creating a number of the mask patterns 201 or the window patterns, thereby improving the efficiency in detection.

Figure 24:
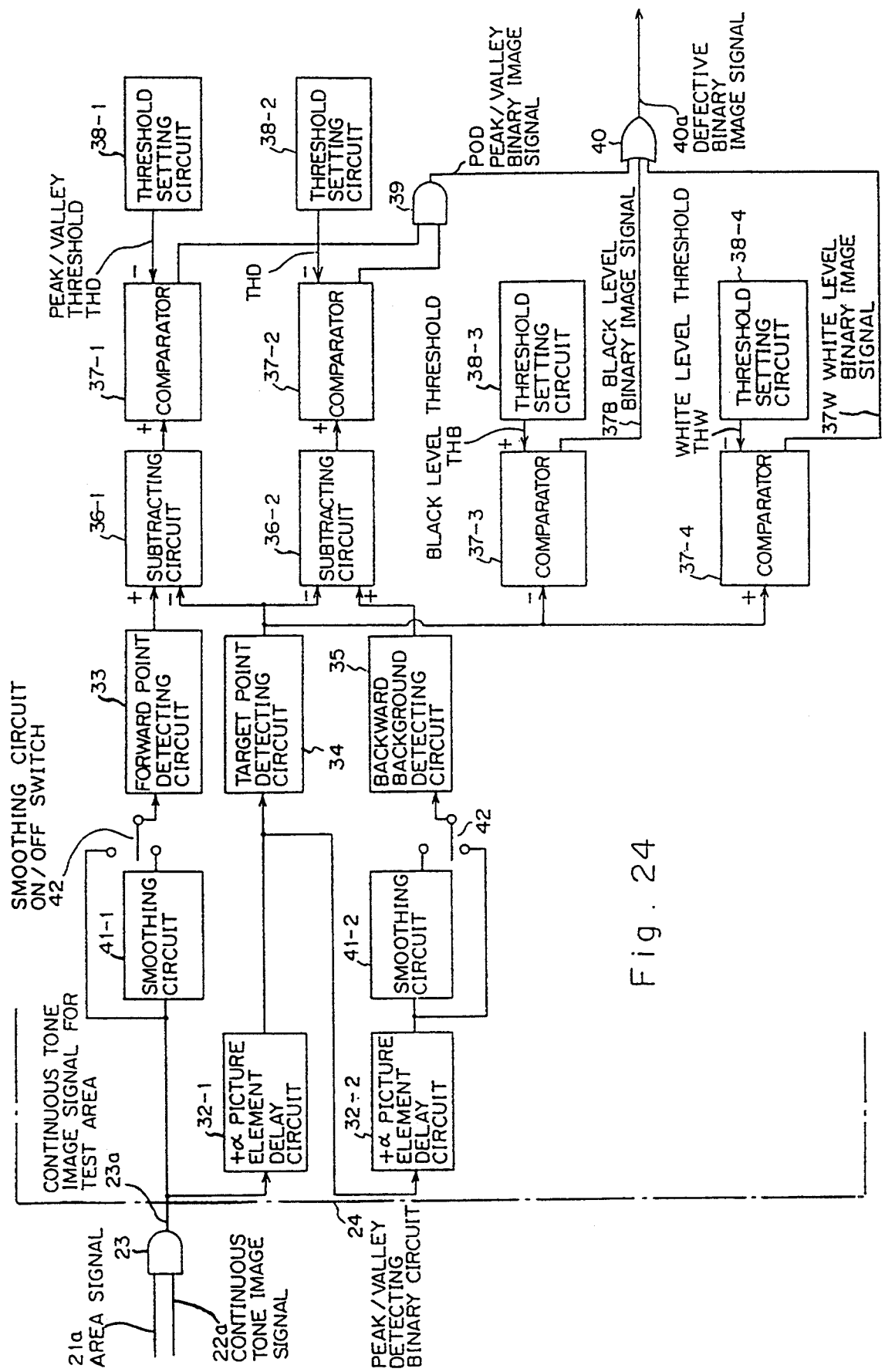
FIG. 24 is a block diagram for explaining in detail the configuration of the peak/valley detecting circuit in an embodiment of the present invention.

FIG. 24 is a block diagram of an embodiment of the detailed configuration of the peak/valley detection and binary-conversion circuit 24 shown in FIG. 23. However, with this configuration, a valley (defect) is detected. In the case of a peak (defect) detection, the subtraction of subtraction circuits 36-1 and 36-2 is inverted, or an input image signal 23a applied to the peak/valley detection and binary-conversion circuit 24 is inverted. In this case, the function of a comparator 37-3 (black level determination by a fixed binary conversion) and that of a comparator 37-4 (white level determination by a fixed binary conversion) are exchanged with each other.

Next, the function shown in FIG. 24 is explained below. FIG. 24 shows the execution of the principle shown in FIG. 23. In FIG. 24, +picture element delay circuits 32-1 and 32-2 sequentially delay an input image signal 23a (that is, a test area continuous tone image signal outputted by the AND gate 23 shown in FIG. 23) by picture elements in the scanning direction.

Smoothing circuits 41-1 and 41-2 smooth an image signal if necessary to reduce the influence of noises; and a smoothing circuit ON/OFF switch 42 switches ON or OFF the smoothing function.

The smoothing circuit 41-1 is provided corresponding to the forward background point detecting circuit 33, and likewise, the smoothing circuit 41-2 is provided corresponding to the backward background point detecting circuit 35. For the purpose of improving the sensitivity in detecting a defect in a target point (that is, improving the function of detecting a picture image indicating a defect by a small peak/valley or small intensity variations, namely, by a small threshold value), the smoothing circuit is not provided for a target point detecting circuit 34 described later.

A forward background detecting circuit 33 receives as an original input image signal a test area continuous tone image signal 23a or a smoothed signal for it to detect a forward background point. A target point detecting circuit 34 receives an output image signal of the +picture element delay circuit 32-1 to detect a target point. A backward background detecting circuit 35 receives an image signal outputted by the + picture element delay circuit 32-2 or a smoothed signal for it to detect a backward background point. Each of the detecting circuits 34, and 35 simultaneously latches the picture element values PO(i+$\alpha$,j), PO(i,j), and PO(i-$\alpha$, j) described by referring to FIG. 22 if the smoothing circuit 41-1 and 41-2 are omitted (that is, the smoothing circuit is short-circuited by the switch 42) when the delay circuits 32-1 and 32-2 are used.

When the smoothing circuits 41-1 and 41-2 are used, the above described picture element values PO(i+$\alpha$,j) and PO(i-$\alpha$,j) are replaced with the results of the following expressions (3) and (4) respectively.

$$PO(i+\alpha,j)=\{k=O^{\Sigma n-1}PO(i+\alpha+k,j)\}/n \qquad (3)$$

$$PO(i-\alpha,j)=\{k=O^{\Sigma n-1}PO(i-\alpha-k,j)\}/n \qquad (4)$$

That is, the smoothing circuit 41-1 replaces the picture element value of the forward background point with an average value of n forward picture element values including the picture element value PO(i+$\alpha$,j) of the forward background point and those of the points beyond it. Likewise, the smoothing circuit 412 2 replaces the picture element value of the backward background point with an average value of n backward picture element values including the picture element value PO(i-$\alpha$,j) of the backward background point and those of the points beyond it.

The average values are not calculated with the background point set as a median to prevent the picture element value PO(i,j) of a target point from being involved in calculating the average values.

An average value obtained by expression (3) or (4) can be replaced with a median in n picture element values (that is, the value at the middle point when n values are arranged in order).

Each piece of the above described image data latched by the detecting circuits 33, 34, and 35 shown in FIG. 24 are applied to the subtracting circuits 36-1 and 36-2 and the difference is calculated according to the contents of expressions (1) and (2) shown in FIG. 22. The difference is compared by comparators 37-1 and 37-2 with a peak/valley value THD each being predetermined by threshold setting circuits 38-1 and 38-2. Thus, a peak/valley binary image signal POD shown in FIG. 22 (a defective valley in this case) can be obtained as an output from the AND gate 39 for ANDing the comparators 37-1 and 37-2.

The comparators 37-3 and 37-4 detect a picture element indicating a defect in a relatively large area. The comparator 37-3 receives image data of a target picture element outputted by the target point detecting circuit 34 which does not receive a smoothed image signal. Then, it compares the received data with a black level threshold THB determined by the threshold setting circuit 38-3, and detects and outputs a black level binary image signal 37B indicating a picture element of a black level defect.

Likewise, the comparator 37-4 receives data of a target picture element, compares it with a white level threshold THW determined by a threshold setting circuit 38-4, and detects and outputs a white level binary image signal 37W indicating a picture element of a white level defect.

An OR gate 40 ORs the signals thus detected as defect-indicating picture element detection signals including a peak/valley binary image signal POD, a black level binary image signal 37B, and a white level binary image signal 37W, and outputs a defect-indicating binary image signal 40a.

A black level defect-indicating picture element detector (the comparator 37-3, etc.) and a white level defect-indicating picture element detector (the comparator 37-4, etc.) operate concurrently with the peak/valley detector/binary-converter (an AND gate etc.). These units separately test an image, and the results are finally put together and outputted as final determination.

Next, an image scanning method is explained below. FIG. 22A shows the continuous tone of an image at a section Q-Q1. In expressions (1), (2), (1A), and (2A), a means the number of picture elements, and is a parameter indicating the frequency of an image signal at a defective portion (that is, the width of a peak or a valley). However, as shown in FIG. 22A, continuous tone image signals for the inner surface of a non-defective container complexly comprise various frequency components. Therefore, the inner surface of a container must be divided if necessary and each of them must be assigned an optimum parameter.

However, the intensity variations in background picture elements can be simplified by appropriately determining the scanning direction of the image, thereby improving the detection precision.

Figure 25A:
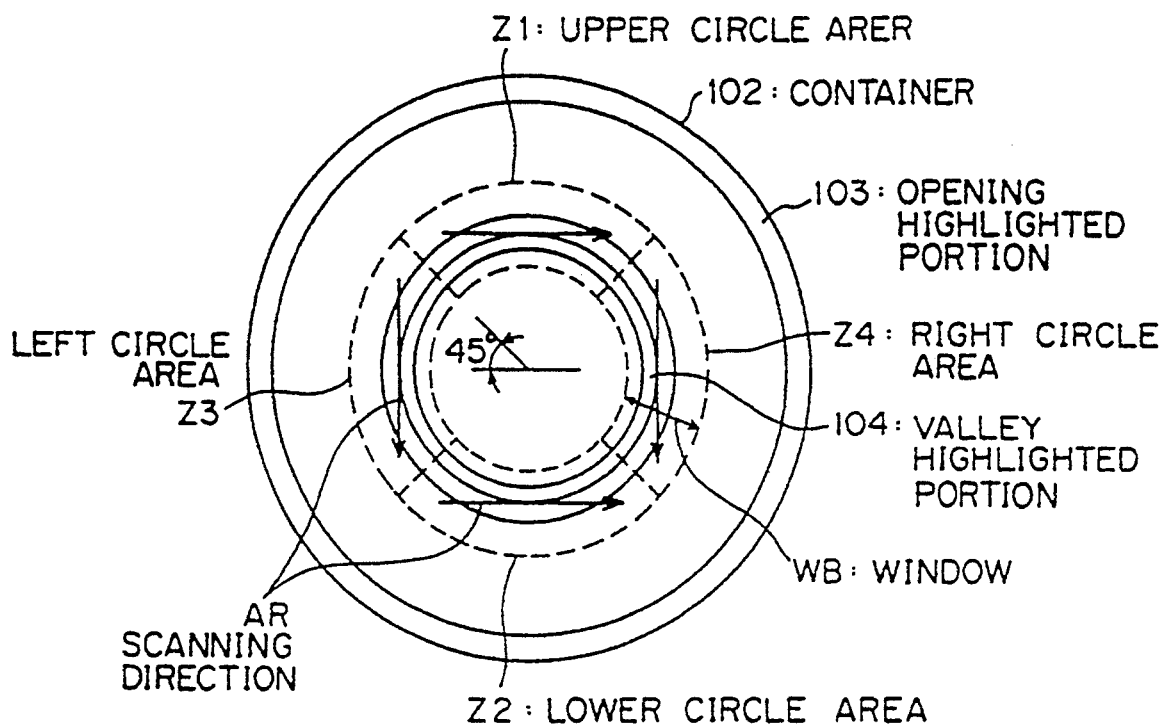
FIGS. 25A-25C show the first embodiment of the screen scanning method of the present invention.
Figure 25B:
Figure 25C:

FIG. 25 is a view for explaining an embodiment of an image scanning method, where a window WB is divided into the following four areas each being selected as a target area to be searched for a defect; Z1, Z2, Z3, and Z4 are respectively upper circle area, lower circle area, left circle area, and right circle area. That is, in FIG. 25, the highlighted valley portion 104 having complicated intensity variations in the container 102 is selected through the window WB and a peak is detected and binary-converted. If the intensity variations are checked horizontally, for example, in the left circle area Z3 of the window WB, the intensity variations occur at a high frequency in portions such as "HF" shown in FIG. 25C, thereby affecting the detection sensitivity. However, if the left circle area Z3 of FIG. 25A is scanned in the direction indicated by the arrow AR, intensity variations can be obtained at a low frequency as the background as shown in FIG. 25B, while the defective portions are detected at a sufficiently high frequency, thereby improving the detective precision.

Figure 26:
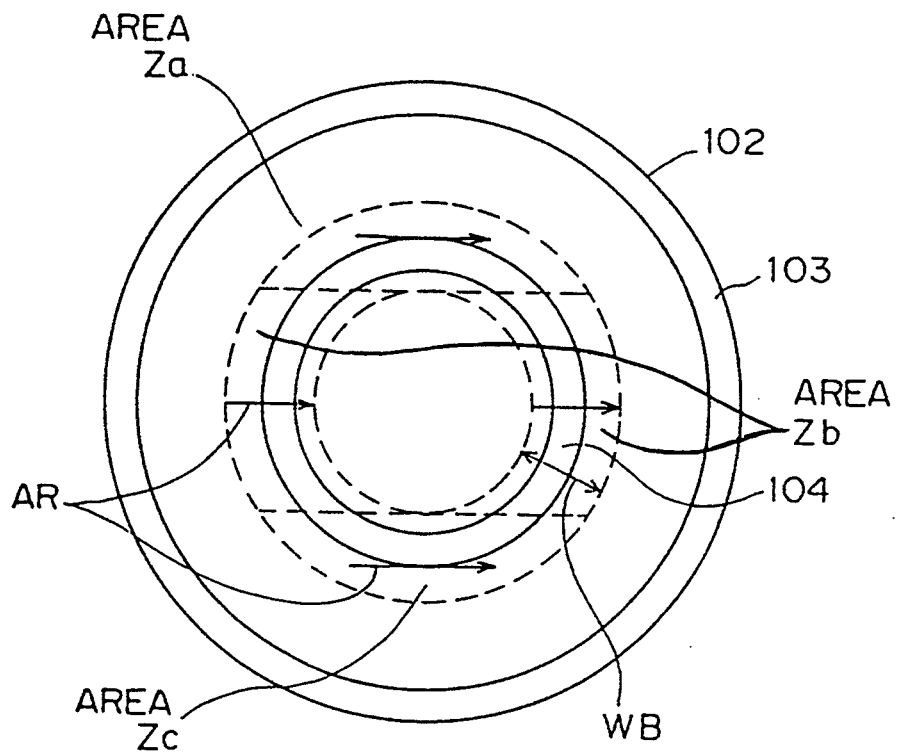
FIG. 26 shows the second embodiment of the screen scanning method of the present invention.

FIG. 26 is a view for explaining an embodiment of a simple picture scanning method. In FIG. 20, an image is scanned horizontally as indicated by the arrow AR, and the window WB is divided into three areas Za, Zb, and Zc. In this case, a threshold for detecting a peak/valley in the areas Za and Zc and a threshold for detecting a peak/valley in the area Zb are determined separately to perform an optimum detection according to the frequency of the background intensity.

In this case, the defect detection sensitivity is low in the area Zb. However, the detection sensitivity in the areas Za and Zc can be enhanced.

Figure 27:
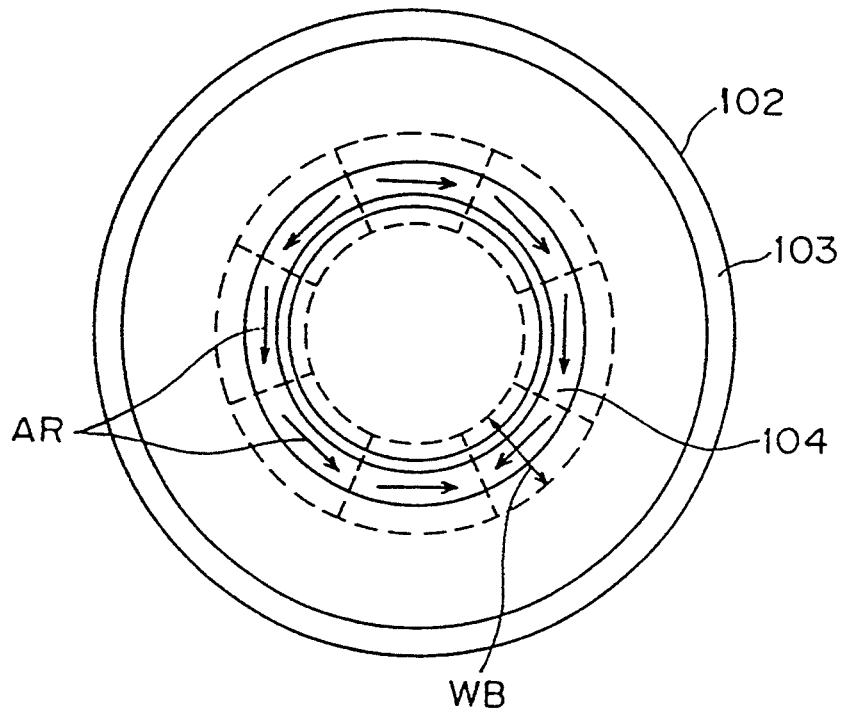
FIG. 27 shows the third embodiment of the screen scanning method of the present invention.

FIG. 27 shows a variation of the embodiment shown in FIG. 25. In FIG. 25, the scanning area is radially and equally divided into four fan-shaped areas. By contrast, in FIG. 27, the area is equally divided into eight fan-shaped areas, and an optimum scanning direction AR is assigned respectively, thereby improving the detection sensitivity much more than the case in FIG. 25.

Figure 28A:
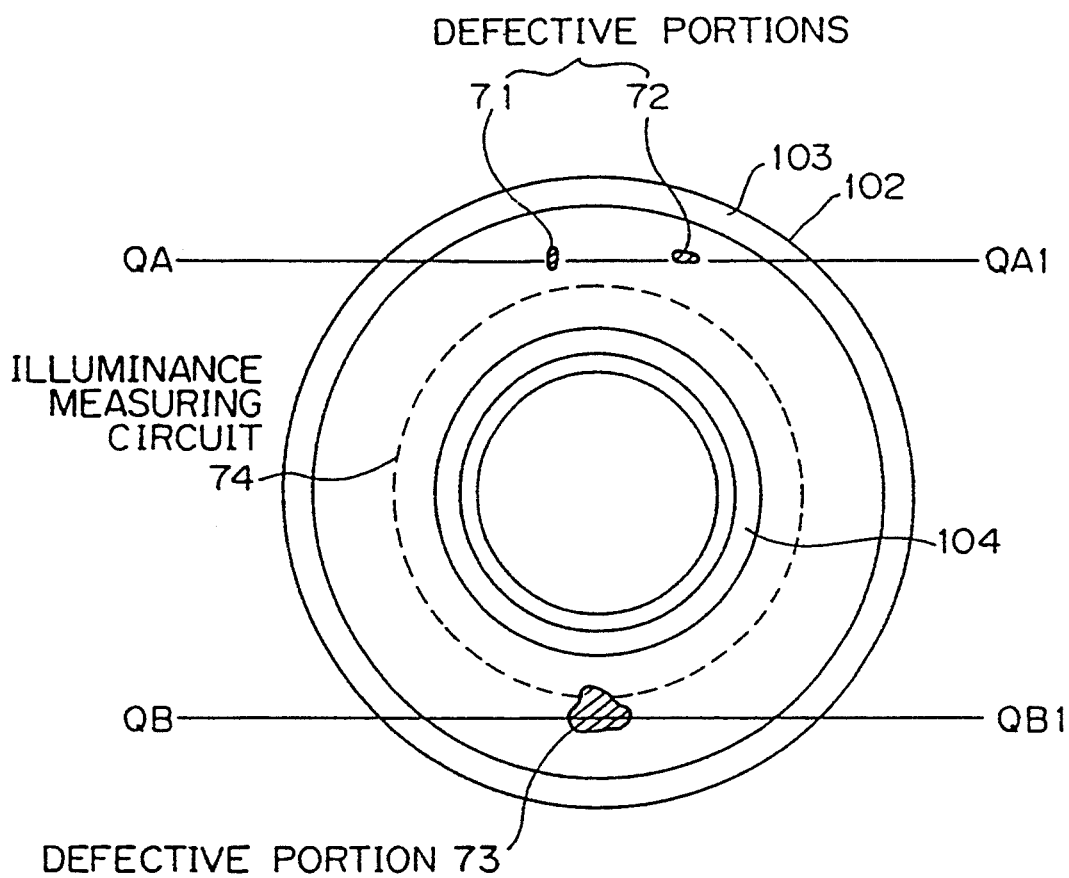
FIGS. 28A-28C show the relationship between the defect detecting method of the present invention and the shape of a defective portion.
Figure 28B:
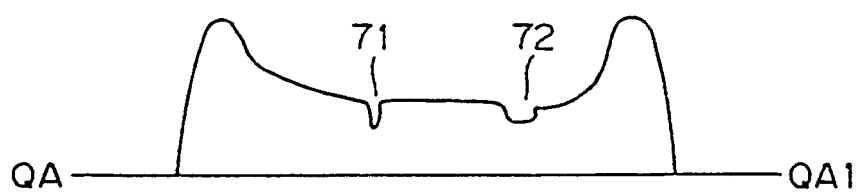

FIG. 28 is a view for explaining the relationship between a defect detecting method based on the present invention and the shape of a defective portion. In FIG. 28A, defective portions 71–73 is detected in the image of the container 102. FIG. 28B shows the intensity variations in the scanning line QA-QA1 shown in FIG. 28A. Defective oval portions 71 an 72 show different intensity frequencies depending on the direction of their longer diameter. Therefore, the defect detection sensitivity can be improved by capturing the amount corresponding to the number $a$ of picture elements in expressions (1) and (2) several times and repeating the check.

Figure 28C:
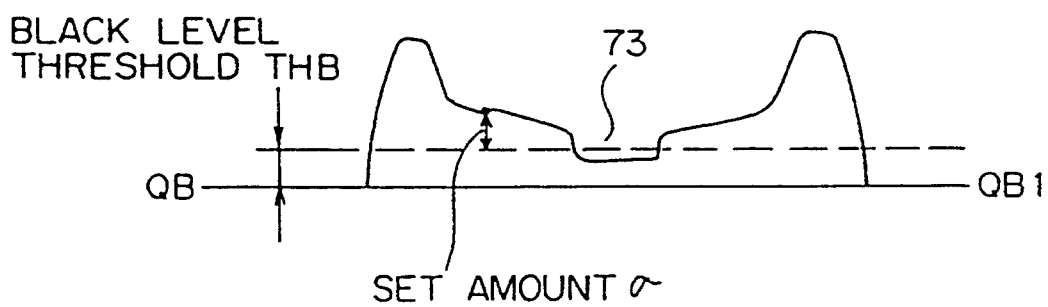
Figure 29:
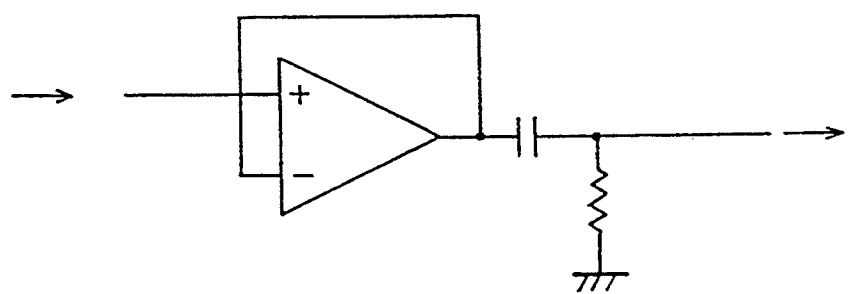
FIG. 29 shows an example of an analog differentiation circuit.

FIG. 28C shows the intensity variations in the scanning line QB-QB1 shown in FIG. 28A. A defective portion 73 in this section is relatively large, and the variation in the continuous image signal is represented at a low frequency but sufficient to detect a black spot in contrast with its background. Since the defective portion 73 must be detected at a low frequency, it cannot be successfully detected unless the number $a$ of the above described picture elements is unpractically large enough in the valley-detection and binary-conversion process. In such a case, using the fixed binary conversion method shown in FIG. 24, a defective portion 73 is isolated and detected as a black level as shown in FIG. 28C by setting a black level threshold THB by the threshold setting circuit 38-3 shown in FIG. 24, thereby supplementing the detective sensitivity in the valley-detection and binary-conversion process.

A black-level threshold THB can be determined by, for example, obtaining an average value of picture element intensity data of a circumference (an illuminance measurement circle) such as a circumference 74 shown in FIG. 28A, and subtracting a predetermined amount a from the average value.

The present invention performs a circularity test on the highlighted portions of the inner surface of a container. As a result, not only the deformation of a container or an abnormal concave in it, but the dust attracted to a highlighted portion of it can be detected with a high detective precision. Accordingly, a large window area can be scanned at a time (that is, the number of windows can be reduced) by parallelly performing the circularity test and the black/white spot test by the conventional defect test method, thereby speeding up the whole process.

The present invention performs a circularity test on a highlighted portion of the inner surface of a container after specifying the position of the container by obtaining the coordinates of the middle point between the first rise point and the last fall point in the scanning line of the binary image of the highlighted opening portion of a container. As a result, not only the deformation of a container (can) or an abnormal concave in it, but the dust attracted to a highlighted portion of it can be detected with a high detective precision. Accordingly, a large window area can be scanned at a time (that is, the number of windows can be reduced) by parallelly performing the circularity test and the black/white spot test by the conventional defect test method, thereby speeding up the whole process.

The present invention specifies the position of the container by obtaining the coordinates of the middle point between the first rise point and the last fall point in the scanning line of the binary image of the highlighted opening portion of a container.

Then, it performs a circularity test on a highlighted portion of an inner surface of a container after obtaining the projected amount of a binary image of the highlighted opening portion (the projection being made in the direction perpendicular to the container adjacent direction), searching from the inner side to the outer side of a container for the difference in the projected amount, detecting adjacent points on a predetermined condition, and isolating a target area from the area containing adjacent containers. As a result, not only the deformation of a container or an abnormal concave in it, but the dust attracted to a highlighted portion of it can be detected with a high detective precision. Accordingly, a large window area can be scanned at a time (that is, the number of windows can be reduced) by parallelly performing the circularity test and the black/white spot test by the conventional defect test method, thereby speeding up the whole process.

The cylindrical container inner surface tester illuminates from above in the axis direction of a container by a ring illumination 101 the inner surface of an axis-symmetrical cylindrical container 102. A TV camera captures the illuminated area of the cylindrical container 102 from above in the axis direction. Then, the captured image is analyzed to determine a black or white spot inside the cylindrical container 102.

The cylindrical container's inside surface tester comprises a defective peak/valley determiner (for example, an antecedent of an AND gate in a peak/valley detection and binary-conversion circuit 24), an image test area divider, and a value changer.

The defective peak/valley determiner determines that a target picture element indicates a defect if two differences obtained by subtracting the value PO(i,j) of a target picture element in the same picture element scanning line for a continuous tone image signal 23a which is obtained by scanning the above described captured image from the values PO(i+α,j) and PO(i-α,j) of two background picture elements (hereinafter referred to as a forward background picture element and a backward background picture element respectively) a predetermined number α of picture elements (hereinafter referred to as α picture elements) backward or forward of the target picture element indicate the same polarity, if an absolute value of one of the above described two differences is larger than a predetermined first threshold (THD, for example) corresponding to the polarity, and if the other absolute value is larger than a predetermined second threshold (THD, for example).

The divider divides (into Z1–Z4, Za–Zc, etc.) the test area of a target image of the defective peak/valley determiner according to the optical features of a cylindrical container inner surface illuminated by the above described illuminator.

The value changer changes at least one value among the number of the above described α picture elements, the first threshold, and the second threshold.

The cylindrical container inner surface tester further comprises a unit for repeating the process performed by the defective peak/valley determiner by changing the number of α picture elements for one of the above described test areas.

The cylindrical container inner surface tester further comprises a black level defect determiner (a comparator 37-3, etc.) for determining a picture element indicating a defect whose continuous tone image signal 23a has a value smaller than a black level threshold THB, a third threshold predetermined for each test area.

The cylindrical container inner surface tester further comprises a white level defect determiner (a comparator 37-4, etc.) for determining a picture element indicating a defect whose continuous tone image signal 23a has a value larger than a white level threshold THW, a fourth threshold predetermined for each test area.

The cylindrical container inner surface tester further comprises a unit for obtaining a complement of 1 or 2 for the continuous tone image signal 23a to generate an inverted continuous tone image signal, converting the signal to the continuous tone image signal 23a, and providing it for the defective defect determiner, thereby detecting a picture element having a white level defect through the black level defect determiner.

The cylindrical container inner surface tester further comprises a unit for selecting for each test area the direction AR which allows the lowest possible frequency in the variation of a continuous tone image signal among a plurality of predetermined image scanning directions such as horizontal, vertical and oblique directions.

The cylindrical container inner surface tester further comprises a smoothing circuit 41-1 for outputting as the value of the above described forward background picture element an average value of the values of picture elements in a section comprising a first predetermined number (n, for example) of picture elements containing the above described forward background picture element in the above described scanning line, and a smoothing circuit 41-2 outputting as the value of the above described backward background picture element an average value of the values of picture elements in a section comprising a second predetermined number (n, for example) of picture elements containing the above described forward background picture element in the above described scanning line.

Since the cylindrical container inner surface tester comprises the above described two units which output a median of the values of picture elements in a corresponding section instead of the above described average value, it can correctly detect a defect even though uneven illuminance is caused by highlighted portions illuminated by an illuminator inside a cylindrical container.

Figure 32:
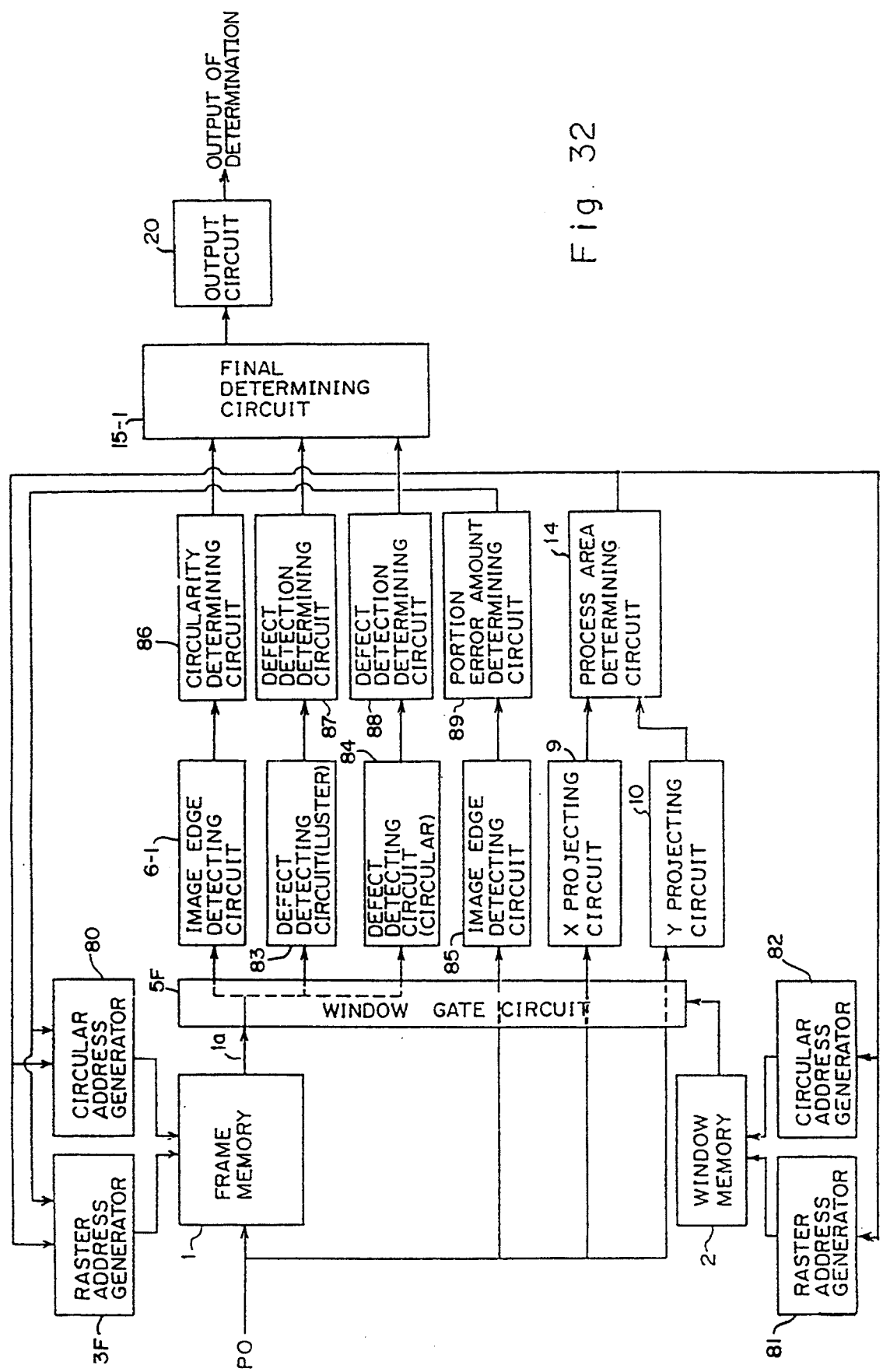
FIG. 32 is a block diagram of the hardware configuration of an embodiment of the present invention.

Next, FIG. 32 is the block diagram of the hardware of the other embodiment of the present invention. In FIG. 32, a continuous tone image signal PO consisting of 8 bits, for example, is obtained by A/D converting a video signal generated by raster-scanning the screen of a TV camera (not shown in FIG. 32); a frame memory 1 receives the multi-value continuous tone image signal PO and stores it as multi-value screen data; a raster address generator 3F generates a raster address for the frame memory; a circular address generator 80 generates an address for the frame memory 1 to circularly scan an image at; a window memory 2 stores a ring mask pattern for each window as shown in FIG. 13B; a raster address generator 81 generates a raster address for the window memory 2 in the same way as that performed by the generator 3F; likewise, a circular address generator 82 generates an address for the window memory 2 to circularly scan an image at. With this configuration, the generation of raster addresses and circular addresses can be switched by switching from the generators 3F and 81 to 80 and 82 or vice versa.

A window gate circuit 5F masks a multi-value continuous tone signal PO or an image signal Ia read from the frame memory 1 with the mask pattern data from the window memory 2, and passes an image signal PO or an image signal Ia read from the frame memory 1 in the specified window area only.

An image edge detecting circuit 6-1 has a function of detecting the edge of an image, that is, the outermost points (the points in the outer circumference) and the innermost points (the points in the inner circumference) of the highlighted ring portion. The inputted image signal is converted to a binary representation according to a predetermined threshold used for detecting the position of a target image and testing the circularity, and the coordinates of the rise point and the fall point of the binary signal indicating the image edge are stored in the memory of the image edge detecting circuit. A circuit 86 tests the circularity of a test object according to the coordinates of the points on the outer or the inner circumference detected by the image edge detecting circuit 6-1.

A defect detecting circuit 83 receives through the window gate circuit 5F the image signal Ia read from the frame memory 1 by raster-scanning the image in the frame memory 1, and detects picture elements indicating black spots, etc. A defect detection determining circuit 87 sums up the detected picture elements indicating a defect and determines whether a defect exists. A defect detecting circuit 84 receives through the window gate circuit 5F the image signal Ia read from the frame memory 1 by circularly scanning the image in the frame memory 1, and detects a picture element indicating a defective concave. A defect detection determining circuit 83 sums up the picture elements indicating a defect and determines whether a defect exists. A circuit 15-1 receives the determination results from the circularity determining circuit 86 and the defect detection determining circuits 87 and 88, and obtains the overall determination, and an output circuit 20 outputs a positive or negative defect determination result according to the output determination signal from the overall determination circuit 15-1.

Next, an X projecting circuit 9 obtains an X-direction projecting pattern for a target image using the latest multi-value signal PO passing through the window gate circuit 5F. Likewise, a Y projecting circuit obtains a Y-direction projecting pattern for a target image. A circuit 14 obtains the area of the test container image not adjacent to other container images according to the data outputted by the two projecting circuits 9 and 10.

That is, when a cylindrical container to be tested passes through a predetermined point, a static image of the test container can be captured from above the container using a strobe light or an exposure controlled by a shutter. During the capture operation, the image is transmitted to the X projecting circuit 9 and the Y projecting circuit 10 so as to extract the characteristics of the projected pattern. When a fixed binary image is projected, the projecting circuits 9 and 10 have a function of converting to the binary representation.

Figure 33:
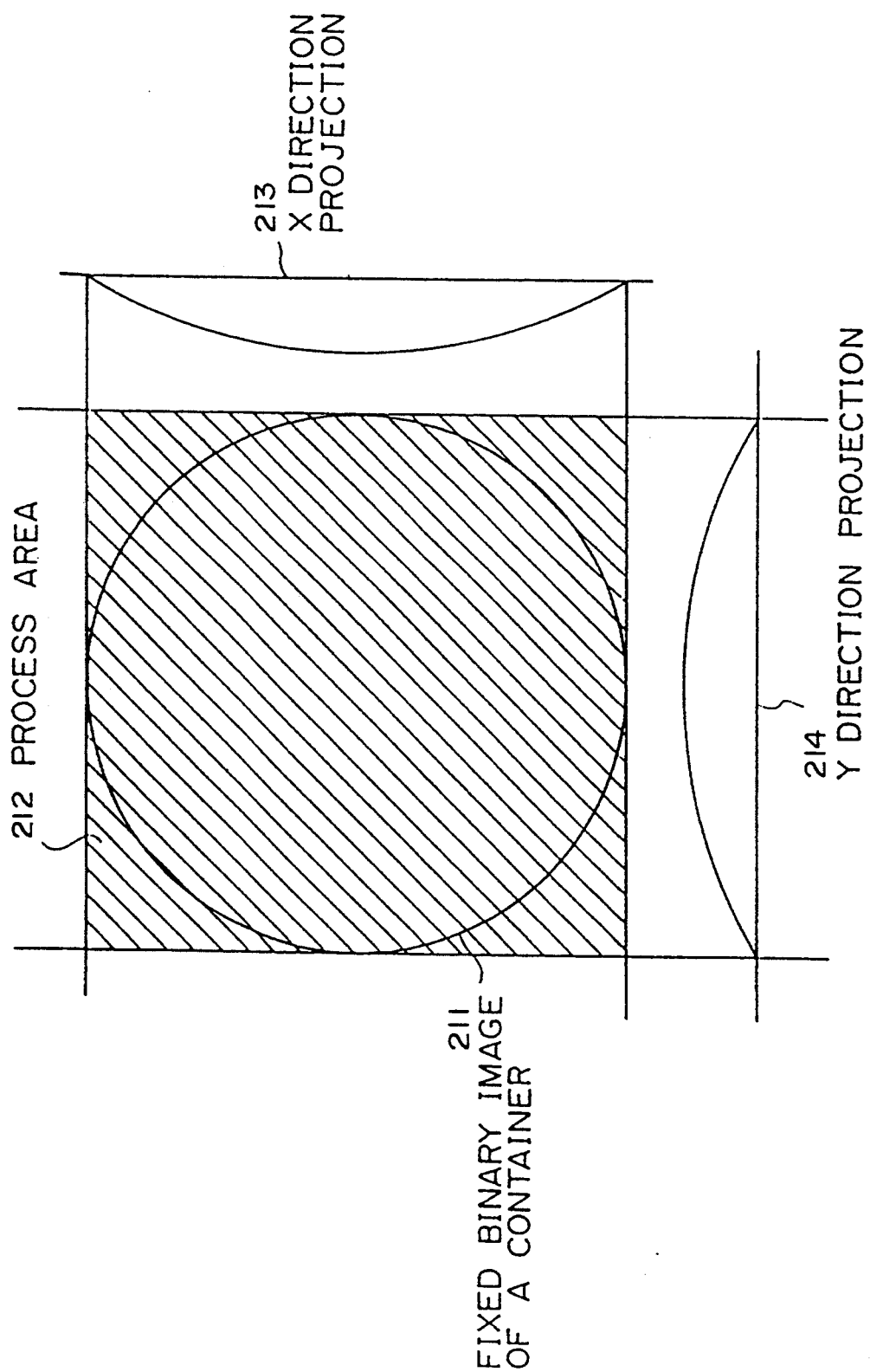
FIG. 33 shows a method of determining the process area for a container.

FIG. 33 shows a method of detecting the bounding rectangle of the container (that is, the process area indicated by diagonal shaded according to the amount of the X-direction projection 213 and the Y-direction projection 214 using the fixed binary image 211 of the container. If containers are carried adjacently on a conveyor, the process area 212 is determined after a process area separation determination circuit 18 separates adjacent containers.

Next, an image edge detecting circuit 85 and a position error amount determining circuit 89 generate a window at a correct position relative to the target image.

Figure 34:
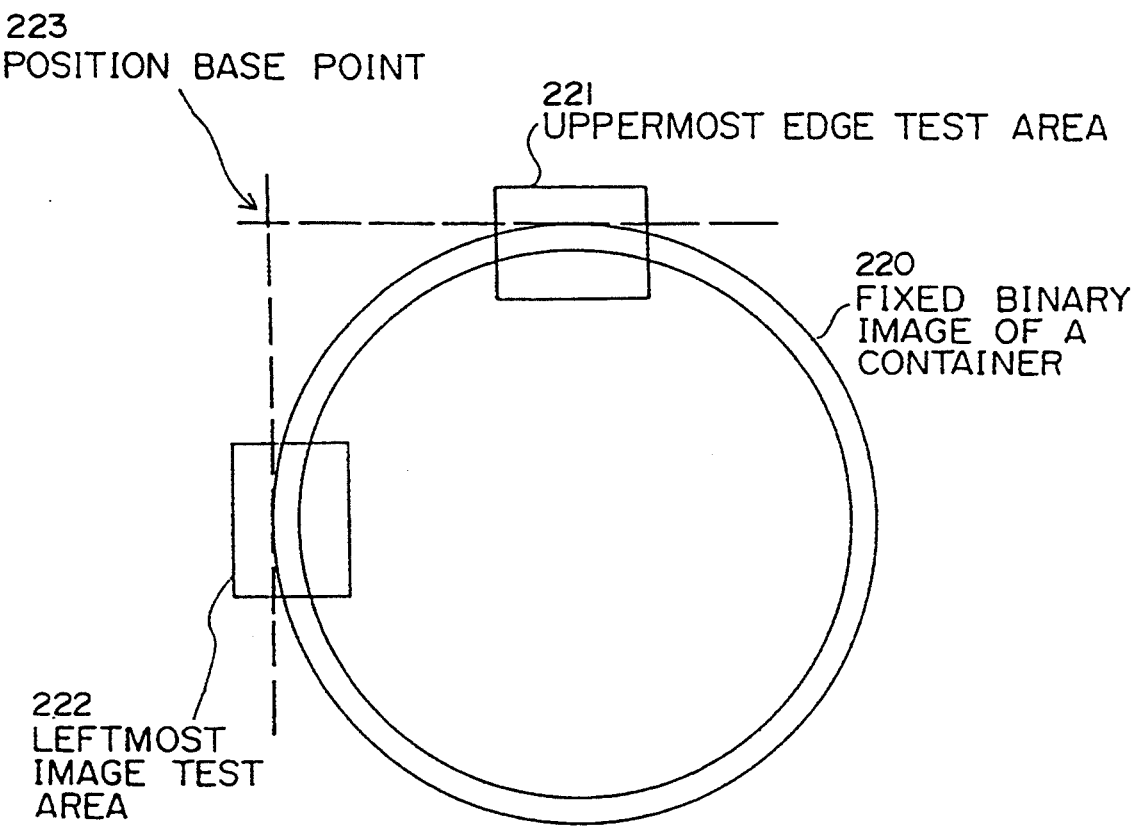
FIG. 34 shows a method of detecting the error in the position of a container.

FIG. 34 shows the operation of the image edge detecting circuit 85. The edge detecting circuit 85 receives the latest multi-value continuous tone image signal PO during the operation of the above described projecting circuits 9 and 10, and generates a fixed binary image 220 of a valley highlighted portion so that the center of the target image can be easily detected. However, the threshold used in this process is generally different from that used by the image edge detecting circuit 6-1.

Then, the coordinates of the edges in a predetermined area for the fixed binary image 220 (in this example, the uppermost edge in the uppermost edge test area 221 and the leftmost edge in the leftmost edge test area 222), that is, the coordinates of the position base point 223 are detected.

The position error amount determining circuit 89 compares the coordinates of the position base point 223 with predetermined base coordinates, and detects the difference between the center position of the currently detected target image and the center position of the predetermined window.

Each of the processes performed by the image edge detecting circuit 6-1, the defect detecting circuit 83, the image edge detecting circuit 85, the X projecting circuit 9, and the Y projecting circuit 10, but not by the defect detecting circuit 84, is performed using the raster address generators 3F and 81. Then, control is transferred to the circular address generators 80 and 82 to generate a circular address and operate the defect detecting circuit 84.

Figure 12A:
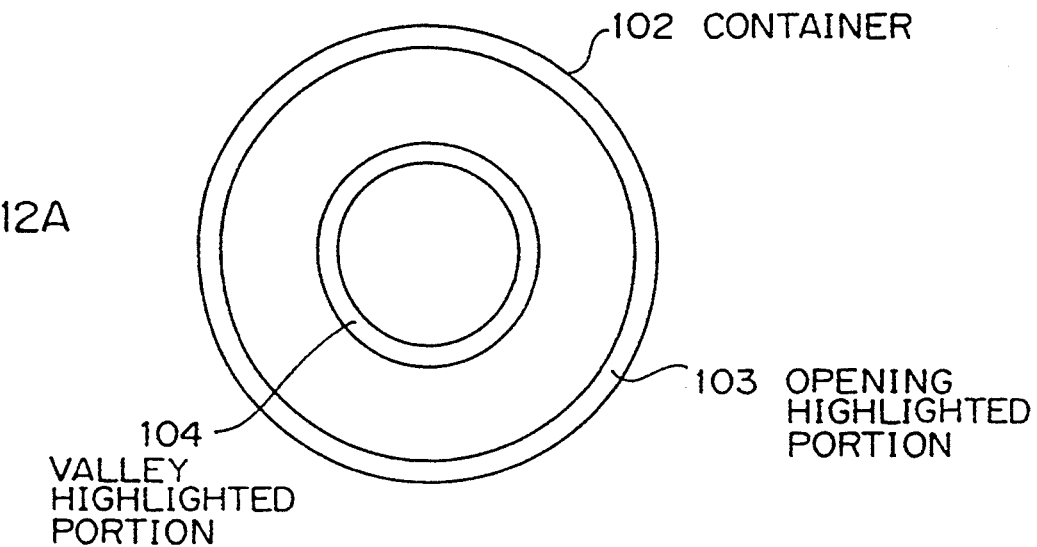
FIGS. 12A and 12B show the highlighted portion inside a container.
Figure 12B:
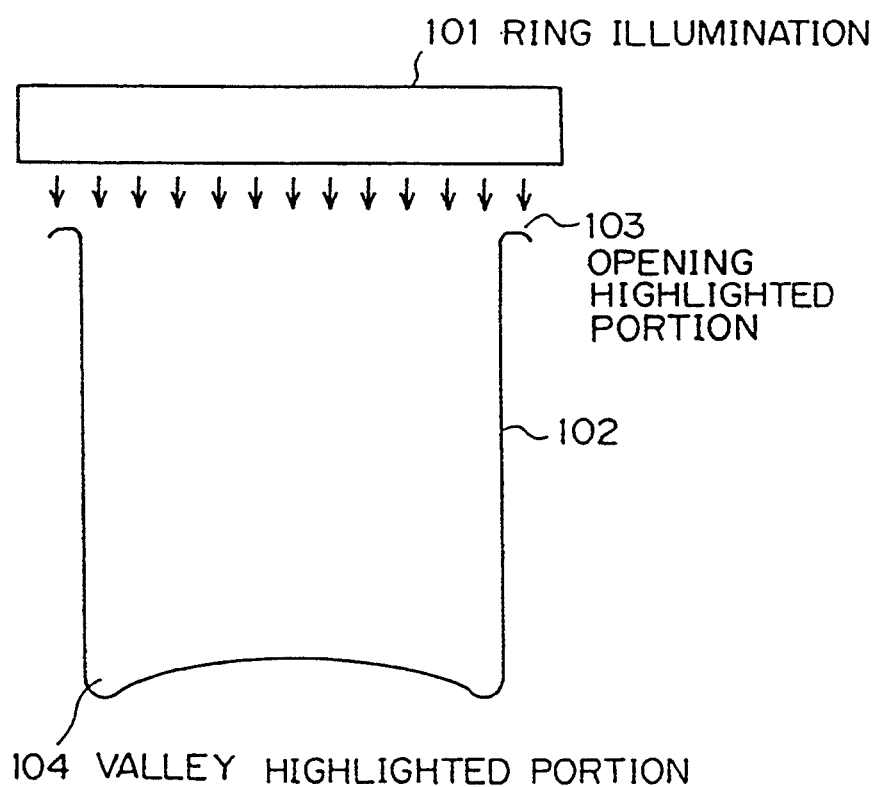
Figure 35:
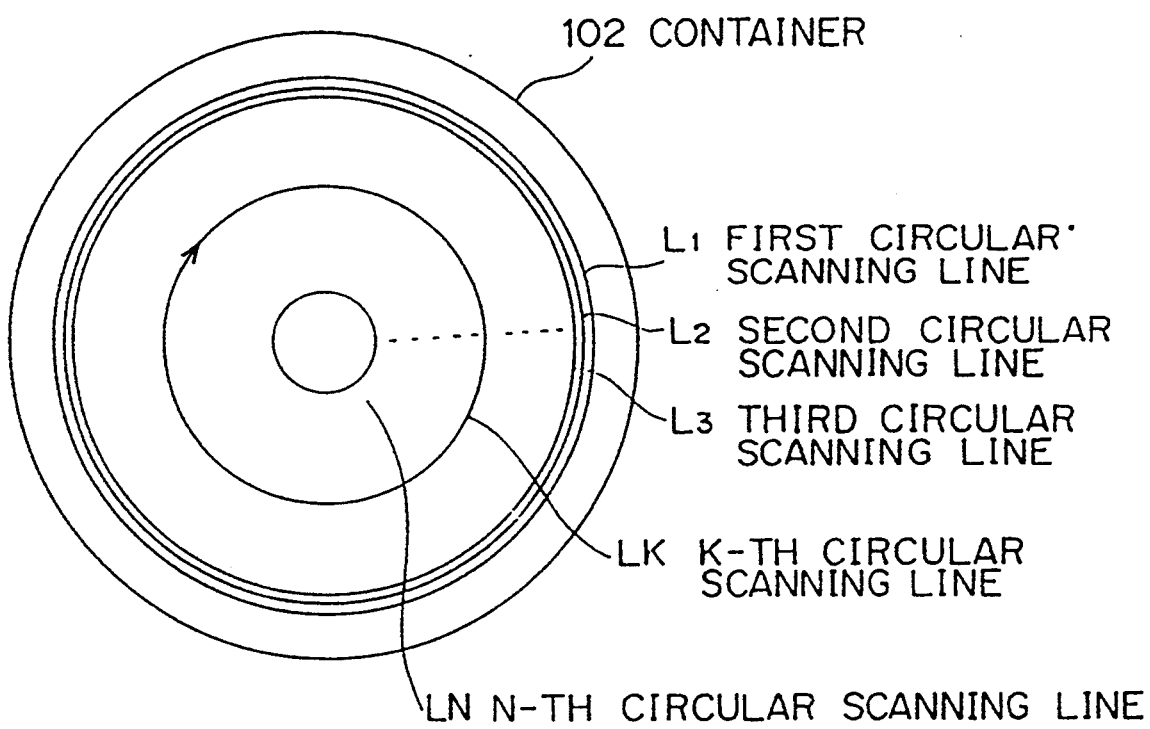
FIG. 35 shows a method of generating a circular address in the present invention.

FIG. 35 shows the method of generating a circular address. In this example, the concentric ring scanning lines (circular scanning lines) L (L1-Ln) are generated for searching the side of the container 102, that is, the image area between the opening highlighted portion 103 and the valley highlighted portion 104 shown in FIGS. 12A and 12B, at intervals of one or more picture element (the interval is determined depending on the size of a defective concave to be detected). The image is circularly scanned clockwise and sequentially for each scanning line L from L1, L2, ... Lk, ... Ln with the scanning lines switched one after another. As described later in FIG. 39, circular addresses are generated such that the X and Y coordinates of target picture elements arranged at every two or more picture elements are specified sequentially in the order of the scanning operation.

Instead of the above described concentric circular scanning lines, the circular scanning lines can be a spiral scanning line in which the scanning radius changes sequentially over each cycle (in this case, the radius gets smaller).

Figure 36:
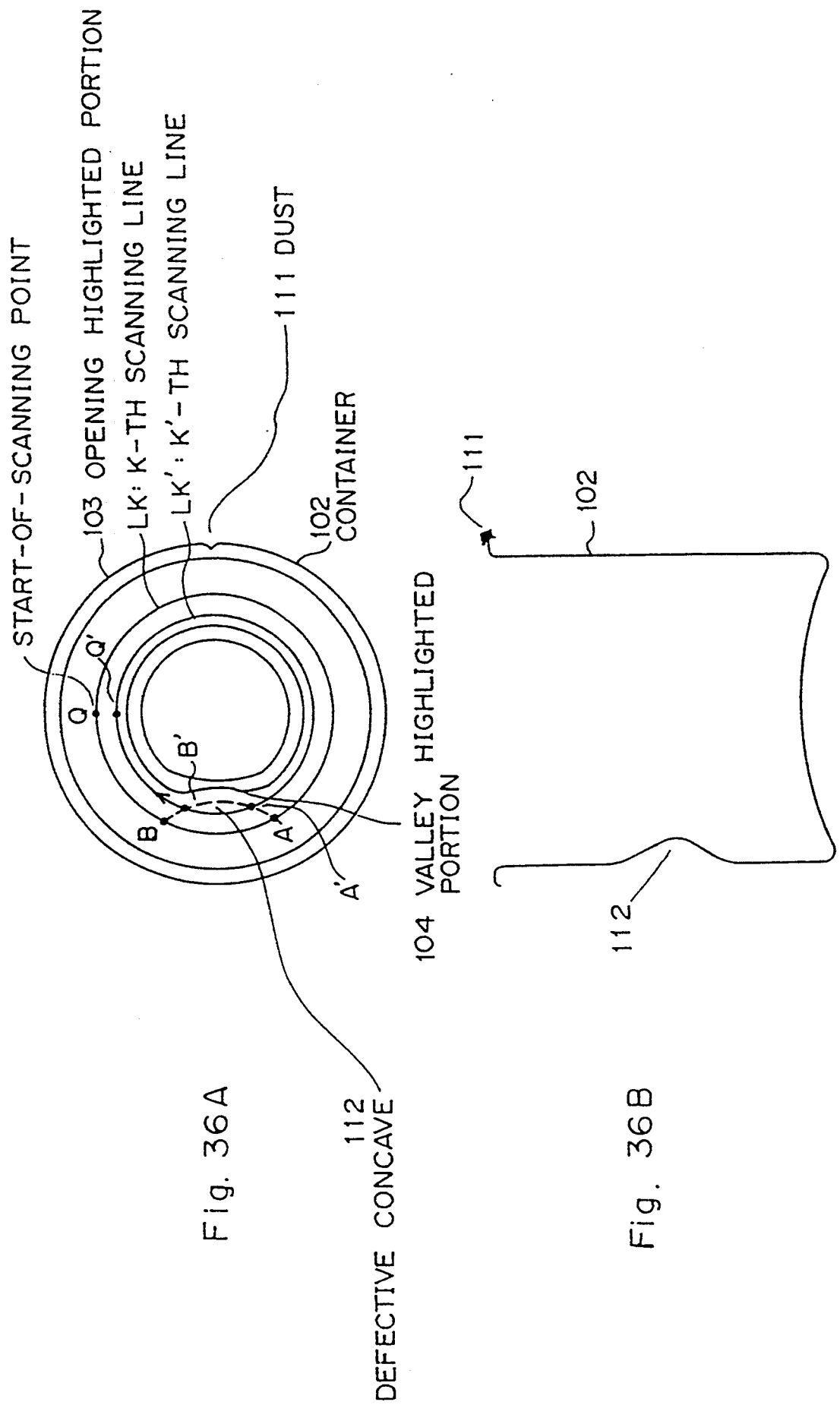
FIGS. 36A and 36B show an example of an image of a container having a concave portion.

FIGS. 36A and 36B show an example of a continuous tone image which indicates that the side of the container 102 shown in FIG. 31B has a defective concave 112. In this case, a defective concave 112 exists between A and B on the k-th scanning line Lk, and between A' and B' on the scanning line Lk' of the circular scanning lines. Points Q and Q' indicate a start-of-scanning point on the circular scanning lines.

Figure 37:
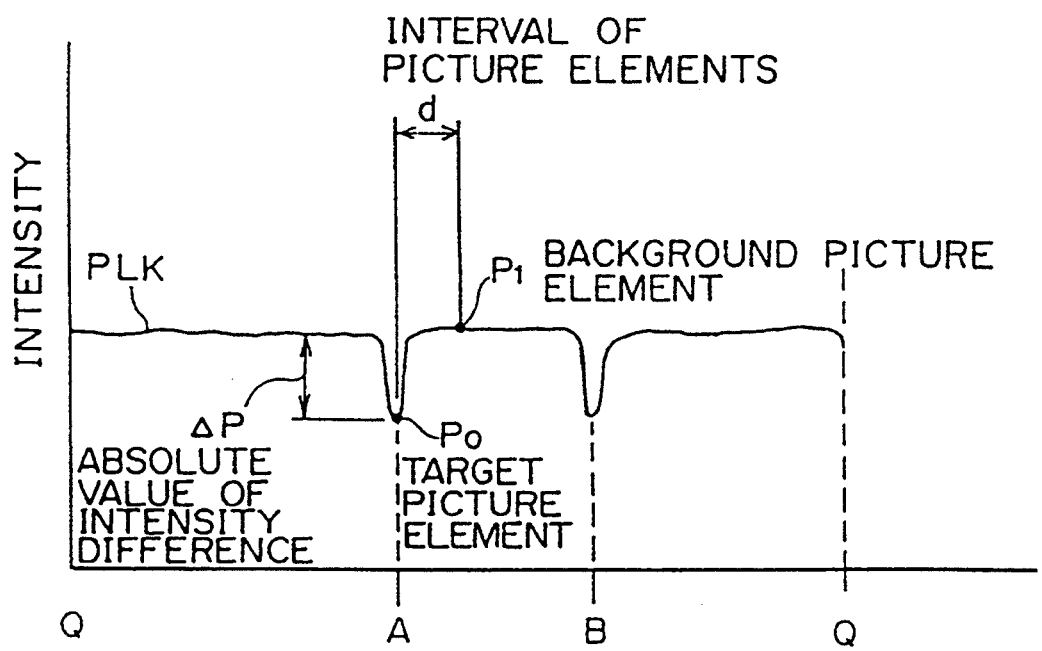
FIG. 37 shows an embodiment of the intensity variations on a scanning line, and shows the principle of the defect detecting circuit based on the circular method shown in FIG.

FIG. 37 shows a view for explaining the principle of the defect detecting circuit 84 of the circular method shown in FIG. 32. PLk shown in FIG. 37 shows an example of intensity variations of the image data on tile k-th scanning line Lk. The characters Q, A, and B on the horizontal axis shown in FIG. 37 corresponds to the characters shown in FIG. 36A. $P_0$ indicates a target picture element and its value, and $P_1$ indicates a background picture element and its value. The background picture element is a predetermined number d of picture elements away from the target picture element.

The defect detecting circuit 84 compares tile threshold THP predetermined for tile window containing the k-th scanning line Lk with the absolute value of the difference between the above described picture element values $P_0$ and $P_1$ calculated as follows.

$$\Delta P = \| P_0 - P_1 \|$$

If $\Delta P > THP$, it is determined that the target picture element $P_O$ indicates a defective inner surface such as a defective concave, etc.

Figure 38:
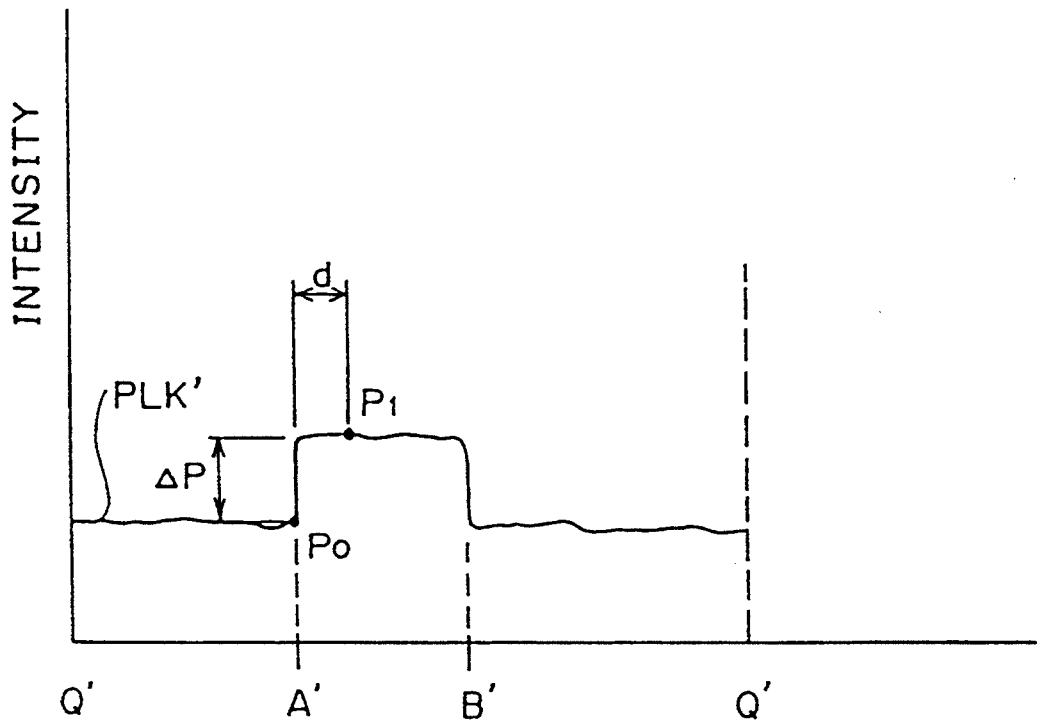
FIG. 38 shows another embodiment of the intensity variations on the scanning line, and shows the principle of the defect detecting circuit based on the circular method shown in FIG.

FIG. 38 shows another view for explaining the principle of the defect detecting circuit 84. PLk' in FIG. 38 shows an example of the intensity variations of the picture element data on the k-th scanning line Lk'. The characters Q', A', and B' on the horizontal axis shown in FIG. 38 correspond to the characters shown in FIG. 36A. The k'-th scanning line Lk' shown in FIG. 36A runs through the low intensity portion existing along outside the valley highlighted portion 104. If a defective concave exists on this portion, the defective concave is highlighted as shown in FIG. 38, and the sign for the intensity difference $P_0$-$P_1$ is inverted from that shown in FIG. 37. However, as shown in FIG. 37, the defect detecting circuit 84 shown in FIG. 38 compares the threshold THP predetermined for the window containing the k'th scanning line Lk' with the absolute value of the difference in intensity variation obtained as follows.

$$\Delta P = \| P_0 - P_1 \|$$

If $\Delta P > THP$, it is determined that the target picture element $P_0$ indicates a defective inner surface such as a defective concave, etc.

Figure 39:
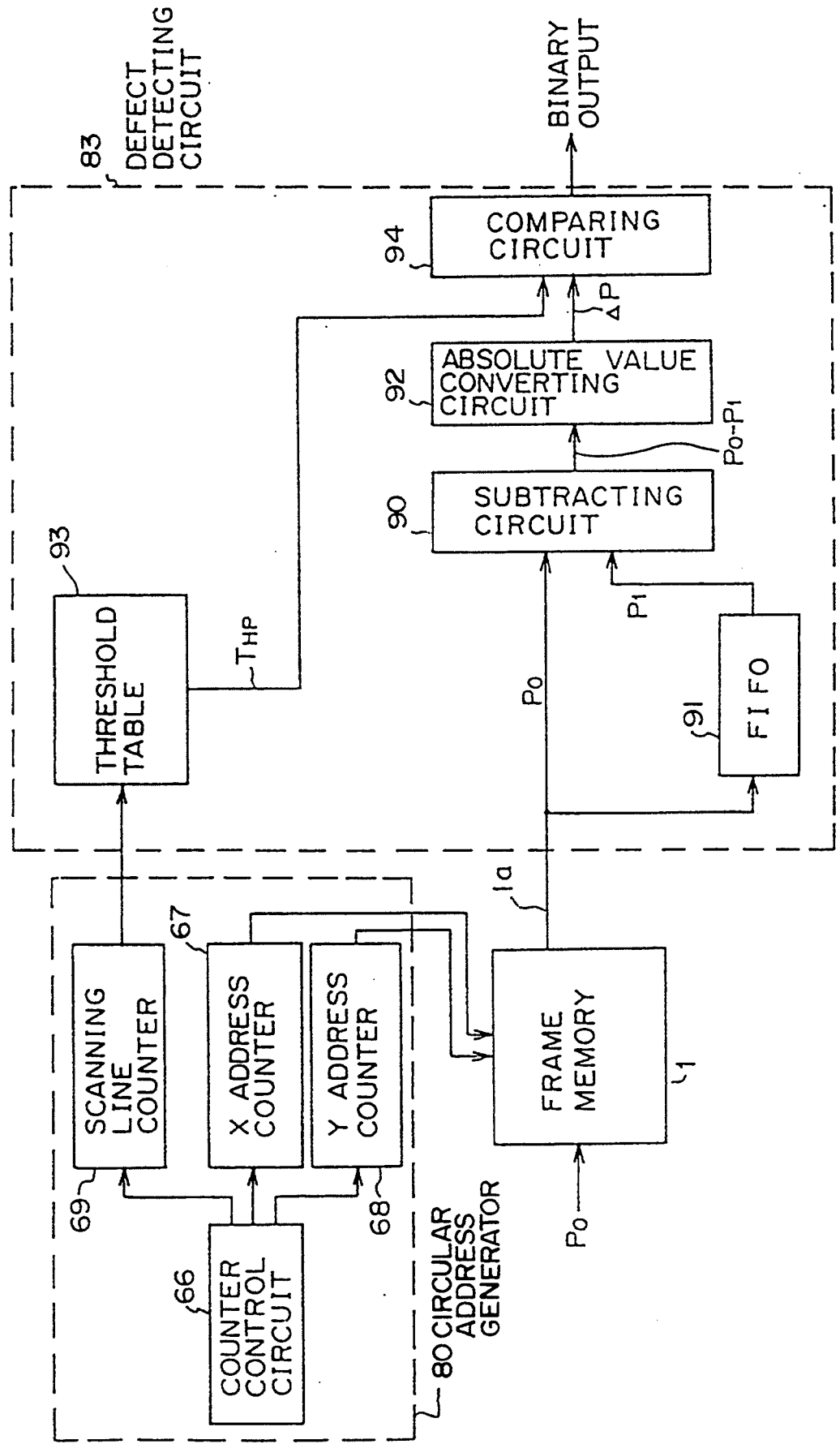
FIG. 39 shows an embodiment of the configuration of the circular address generator and the defect detecting circuit based on the circular method shown in FIG.

FIG. 39 is a block diagram of the configuration of the circular address generator 80 and the defect detecting circuit 94 shown in FIG. 32. The counter control circuit 66 in the circular address generator 80 controls an X address counter 67 and a Y address counter 68 in the circular address generator 80 to sequentially output froth the counters 67 and 68, to the frame memory 1, X and Y addresses as circular addresses of each target picture element in the order of scanning lines L1, L2, ..., Ln shown in FIG. 35. The scanning counter 69 is provided in the circular address generator 4, and the value indicated by the counter 69 is incremented by 1 each time the test image is scanned along one circle.

In the defect detecting circuit 12, a continuous tone image signal (picture element value) 1a read according to the above described circular addresses from the frame memory 1 is sequentially inputted to a subtracting circuit 70 and a FIFO 71. The FIFO 71 delays the inputted image signal 1a by the number d (the above described interval of target picture elements).

Therefore, the subtracting circuit 70 receives the image signal 1a as a value PO of the target picture element shown in FIG. 37, receives a picture element value outputted by the FIFO 71 as a value P1 of the background picture element separate from the target picture element shown in FIG. 37 by the number d (the above described interval of target picture elements), and obtains the difference between them ($P_0$−$P_1$). The absolute value converting circuit 72 obtains the absolute value ($\| P_0 - P_1 \| = \Delta P$) of the difference P0-P1.

The threshold table 73 in the defect detecting circuit 84 outputs a threshold THP according to the address outputted by the scanning line counter 69 (that is, the address for each of scanning lines L1, L2, ..., Ln). At this time, the threshold THP in a window can be set to the same value.

A comparing circuit 94 compares the above described absolute value $\Delta P$ of the difference in intensity with the threshold THP, and outputs a binary conversion signal as the determination of whether or not the target picture element indicates a defective concave, etc., according to whether or not $\Delta P > THP$ exists.

Figure 40:
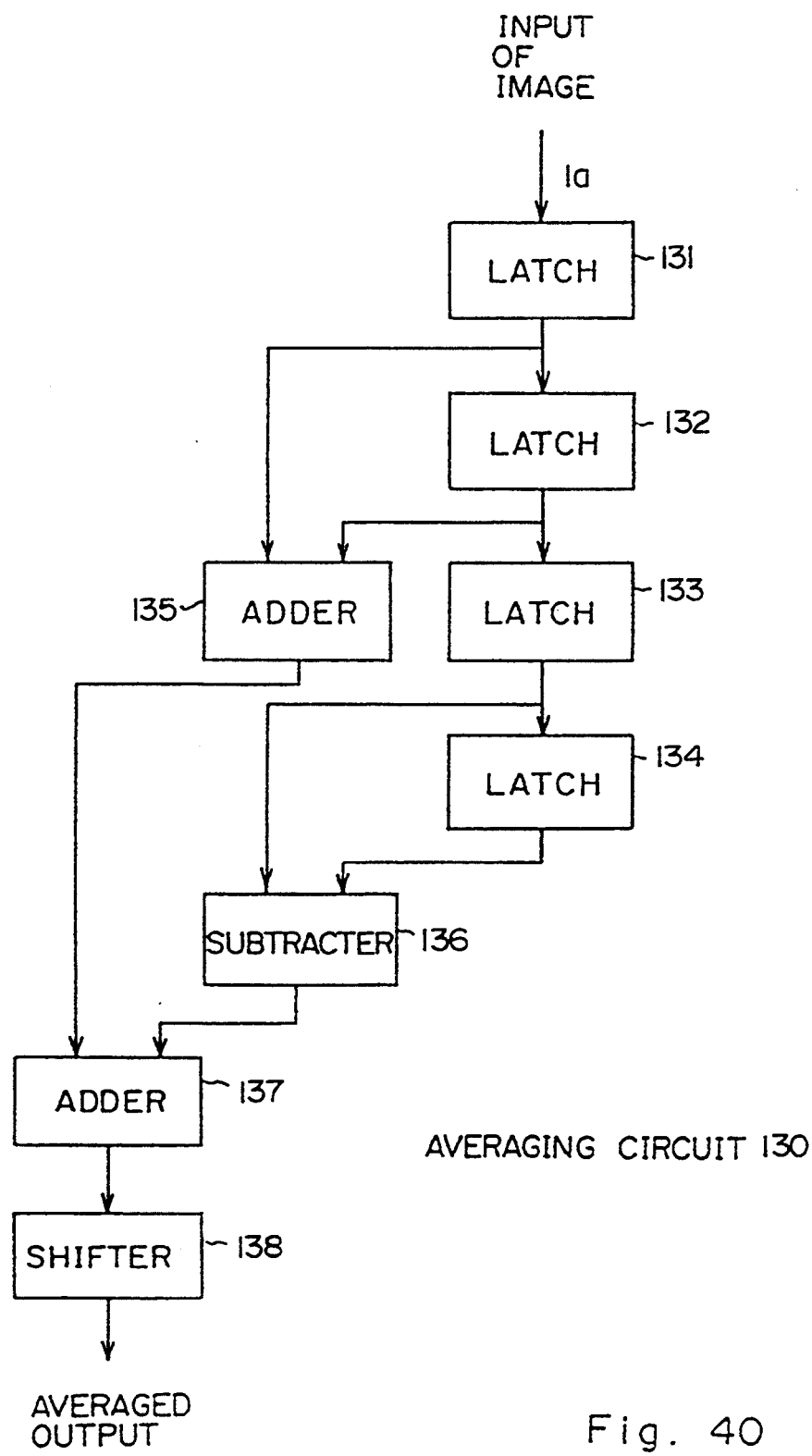
FIG. 40 shows an embodiment of the circuit for applying a moving average to the background picture element values shown in FIG.

FIG. 40 shows an example of the configuration of an averaging circuit 106 for applying a moving average to the picture element value $P_1$ outputted by the FIFO 91 shown in FIG. 39. The circuit 130 is provided in series with the FIFO 91 shown in FIG. 39 (in this example, between the frame memory 1 and the FIFO 91). The averaging circuit 130 calculates the moving average of four picture elements sequentially inputted in series. While an inputted image signal (picture element value) 1a is transmitted to latches 131, 132, 133, and 134 sequentially in this circuit 130, the image data in latches 131 and 132 are added by an adder 135, and the image data in latches 133 and 134 are added by an adder 136. Then, the addition results are added by an adder 137, and thus, the sum of four picture element values is obtained. A shifter 183 calculates an averaged output by shifting the resultant sum by two bits to right (that is, the sum is divided by 4).

Figure 41:
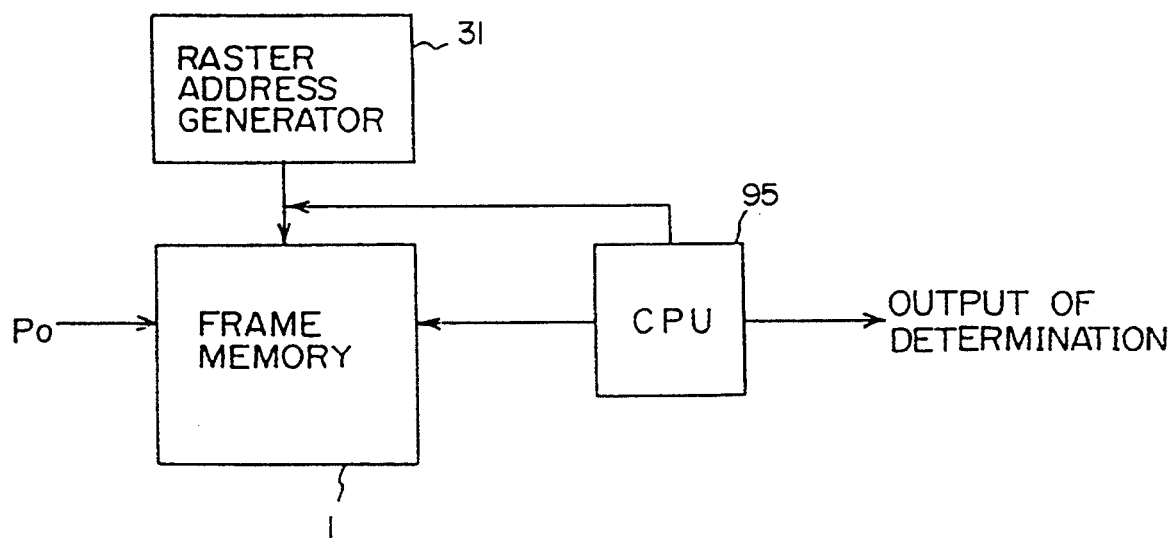
FIG. 41 is a block diagram of an embodiment of the configuration in which circular addresses shown in FIG. 32 is generated by software.

FIG. 41 shows an example in which a CPU 95 replaces using software the functions of the circuit excluding the frame memory 1 and the raster address generator 3F shown in FIG. 32. In this case, since the circular address generating circuits 80 and 82 operating as the hardware for accessing the frame memory 1 are not provided independently, it is supposed that the processing time of the CPU 95 is longer. Therefore, it is required that the processing time of the CPU 95 be shortened and the interval between circular scanning lines L should be appropriately extended, or the interval between target picture elements on the scanning line L should be extended.

Figure 42:
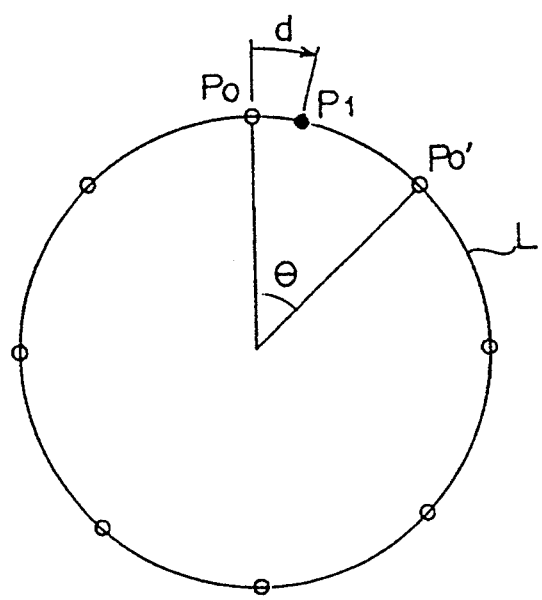
FIG. 42 is an embodiment of the process by the CPU shown in FIG. 41.

FIG. 42 shows an example of shortening the processing time. First, the data of the target picture element $P_0$ on the circular scanning line L are read. Then, the data of the background picture element $P_1$ separated from $P_0$ by the number d of picture elements are read. The absolute value of the intensity difference between the two picture elements is obtained ($\| P_0 - P_1 \|$). Then, the absolute value of the intensity difference is compared with the predetermined threshold THP and the target picture element $P_0$ is converted to the binary representation to determine whether or not the target picture element indicates a defect. If it does not indicate a defect, control is transferred to the next target picture element $P_0'$ separated from the present one by $\theta$, and the above described process is performed on it. The scanning operation completes when all circular scanning lines are processed.

The defect detection determining circuit 88 determines such that the number of picture elements indicating a defect is accumulated over one or more circular scanning lines, the number is compared with a predetermined area threshold, and then it is determined whether or not the inner surface of the test container has a defect.

The average intensity of the picture elements forming a predetermined two-dimensional local area (for example, an area of 3 picture elements×3 picture elements) centered on the background picture element P1 can replace the average intensity of a predetermined number of picture elements (a one-dimensional local area) arranged on the circular scanning line L centered on the background picture element P1 shown in FIG. 40.

With the above described configuration of the cylindrical container inner surface tester, the image of a cylindrical container is scanned along a ring or spiral circular scanning line. Then, the difference in intensity between picture elements arranged at predetermined intervals along the scanning line is obtained. If the absolute value indicating the intensity difference exceeds a threshold predetermined according to the position of the circular scanning line, it indicates a defect of the container's, such as a concave, etc. Therefore, a slight local concave on the side of a cylindrical container can be exactly detected.

What is claimed is:

1. A cylindrical container inner surface tester for illuminating from above an opening of a test container located at a predetermined position with its opening set levelly, for capturing said opening through a TV camera, and for detecting black and white spots on the inner surface if said cylindrical container by analyzing using defect detecting means an image obtained by said TV camera, said tester comprising:
    a frame memory for storing as image data a multi-value contained tone image signal A/D-converted from a continuous tone image signal obtained by scanning said captured image, and
    an area detecting unit for generating a binary image signal by binary-converting using a predetermined threshold (THG) a multi-value continuous tone image signal read by horizontally or vertically scanning the frame memory and for determining as a test area the area between the first rise point and the last fall point oft an image signal depending on the shading of each image obtained by said capturing process from the start to the end of the scanning operation.

2. The cylindrical container inner surface tester according to claim 1 further comprising:
    masking means for masking with predetermined mask pattern data an area having a different optical characteristic in the test area detected by said area detecting unit.

3. A cylindrical container inner surface tester for illuminating from above an opening of a test container located at a predetermined position with its opening set levelly, for capturing said opening through a TV camera, and for detecting black and white spots on the inner surface of said cylindrical container by analyzing using defect detecting means an image obtained by said TV camera, said tester comprising:
    determining means for determining a defect when the image of the inner surface of said cylindrical container is scanned along a ring or spiral scanning line (hereinafter referred to as a circular scanning line) which is centered on the center of the image and varies sequentially per cycle of a radius varying every one or more picture elements predetermined, and then the absolute value indicating the difference between the intensity of the target picture elements among a plurality of picture elements arranged at intervals such that one or more picture elements are arranged between two target picture elements and the intensity of background picture element predetermined number of a plurality of picture elements forward or backward of the target picture element is compared with a threshold predetermined according to the position of the circular scanning line, and such processes are repeated for each target picture element, and said determining means determining a defective container inner surface when an absolute value larger than the value of the difference between said intensity values is detected.

4. The cylindrical container inner surface tester according to claim 3, wherein
    said threshold is set for every cycle of said circular scanning line.

5. The cylindrical container inner surface tester according to claim 3 or 4, wherein
    the intensity of said background picture element equals the average intensity of the picture elements in a predetermined one- or two-dimensional local area centered on said background picture element.

* * * * *

UNITED STATES PATENT AND TRADEMARK OFFICE
CERTIFICATE OF CORRECTION

PATENT NO. : 5,338,000
DATED : August 16, 1994
INVENTOR(S) : Toyama

It is certified that error appears in the above-indentified patent and that said Letters Patent is hereby corrected as shown below:

Column 1, line 32, delete "W8" and insert --W5--.

Column 4, line 48, after "FIG." insert --32--.

Column 4, line 52, after "FIG." insert --32--.

Column 4, line 55, after "FIG." insert --32--.

Column 4, line 58, after "FIG." insert --39--.

UNITED STATES PATENT AND TRADEMARK OFFICE
CERTIFICATE OF CORRECTION

PATENT NO. : 5,338,000
DATED : August 16, 1994
INVENTOR(S) : Toyama

It is certified that error appears in the above-indentified patent and that said Letters Patent is hereby corrected as shown below:

Column 9, line 4, delete "a" and insert --$\alpha$--.

Column 9, line 10, delete "a" and insert --$\alpha$--.

Column 10, line 3, delete PO and insert --$P_o$-$P_i$--.

Column 12, line 6, delete "$X_{k+b}$" and insert --$X_{K+2}$--.

Column 12, line 16, after "b" delete "-" and insert --=--.

UNITED STATES PATENT AND TRADEMARK OFFICE
CERTIFICATE OF CORRECTION

PATENT NO. : 5,338,000  
DATED : August 16, 1994  
INVENTOR(S) : Toyama

Page 3 of 10

It is certified that error appears in the above-indentified patent and that said Letters Patent is hereby corrected as shown below:

Column 13, line 4, after "FIG." insert --3--.

Column 13, line 12, after "window" (first occurrence) insert --W3--.

Column 13, line 14, after "FIG." insert --13.--.

Column 13, line 25, delete "$2" and insert --S2--.

Column 13, line 28, delete "$3" and insert --S3--.

UNITED STATES PATENT AND TRADEMARK OFFICE
CERTIFICATE OF CORRECTION

PATENT NO. : 5,338,000
DATED : August 16, 1994
INVENTOR(S) : Toyama

It is certified that error appears in the above-indentified patent and that said Letters Patent is hereby corrected as shown below:

Column 13, line 29, delete "$\alpha X$" and insert --$\Delta x$--.

Column 13, line 40, delete "$4" and insert --S4--.

Column 13, line 46, delete "$5" and insert --S5--.

Column 13, line 65, delete "$9" and insert --S9--.

Column 14, line 14, delete "SSA" and insert --S5A--.

UNITED STATES PATENT AND TRADEMARK OFFICE
CERTIFICATE OF CORRECTION

PATENT NO. : 5,338,000
DATED : August 16, 1994
INVENTOR(S) : Toyama

It is certified that error appears in the above-indentified patent and that said Letters Patent is hereby corrected as shown below:

Column 14, line 21, delete "DA" and insert --5A--.

Column 14, line 27, after "circuit" insert --13.--.

Column 14, line 37, delete "so" and insert --s6--.

Column 15, line 1, delete "BO" and insert --BC--.

Column 18, line 44, delete "FIG." and insert --Figure 31B--.

UNITED STATES PATENT AND TRADEMARK OFFICE
CERTIFICATE OF CORRECTION

PATENT NO. : 5,338,000
DATED : August 16, 1994
INVENTOR(S) : Toyama

It is certified that error appears in the above-indentified patent and that said Letters Patent is hereby corrected as shown below:

Column 18, line 52, delete "I" and insert --1--.

Column 19, line 5, delete "04" and insert --64--.

Column 20, line 11, before "34" insert --33,--.

Column 20, line 31, delete "412 2" and insert --41-2-

Column 21, line 15, after "gate" insert --39--.

UNITED STATES PATENT AND TRADEMARK OFFICE
CERTIFICATE OF CORRECTION

PATENT NO. : 5,338,000
DATED : August 16, 1994
INVENTOR(S) : Toyama

It is certified that error appears in the above-indentified patent and that said Letters Patent is hereby corrected as shown below:

Column 21, line 20, delete "a" and insert --$\alpha$--.

Column 21, line 55, delete "20" and insert --26--.

Column 22, line 38, delete "a" and insert --$\alpha$--.

Column 24, line 15, delete "defect" and insert --peak/vally--.

UNITED STATES PATENT AND TRADEMARK OFFICE
CERTIFICATE OF CORRECTION

PATENT NO. : 5,338,000
DATED : August 16, 1994
INVENTOR(S) : Toyama

It is certified that error appears in the above-indentified patent and that said Letters Patent is hereby corrected as shown below:

Column 24, line 9, after "area." insert -- The cylindrical container inner surface tester further comprises a unit for obtaining a complement of 1 or 2 for the continuous tone image signal 23a to generate an inverted continuous tone image signal,) converting the signal to the continuous tone image signal 23a, and providing it for the defective peak/valley determiner, thereby detecting a picture element having a defective peak/valley without inverting the above described polarity--.

Column 24, line 15, delete "defective" and insert -- black level--.

UNITED STATES PATENT AND TRADEMARK OFFICE
CERTIFICATE OF CORRECTION

PATENT NO. : 5,338,000
DATED : August 16, 1994
INVENTOR(S) : Toyama

It is certified that error appears in the above-indentified patent and that said Letters Patent is hereby corrected as shown below:

Column 27, line 2, delete "tile" and insert --the--.

Column 27, line 10, delete "tile" and insert --the--.

Column 27, line 11, delete "tile" and insert --the--.

Column 27, line 45, delete "94" and insert --84--.

Column 27, line 49, delete "froth" and insert --from--

UNITED STATES PATENT AND TRADEMARK OFFICE
CERTIFICATE OF CORRECTION

PATENT NO. : 5,338,000
DATED : August 16, 1994
INVENTOR(S) : Toyama

It is certified that error appears in the above-indentified patent and that said Letters Patent is hereby corrected as shown below:

Column 28, line 33, delete "183" and insert --138--.

Column 29, line 32, delete "if" and insert --of--.

Column 29, line 45, delete "bf" and insert --of--.

Signed and Sealed this

Second Day of April, 1996

Attest:

BRUCE LEHMAN

*Attesting Officer*     *Commissioner of Patents and Trademarks*